(12) United States Patent
Jones et al.

(10) Patent No.: US 8,119,615 B2
(45) Date of Patent: Feb. 21, 2012

(54) METHODS AND KITS FOR FOLDING PROTEINS

(75) Inventors: Daniel Brian Jones, Cambridge (GB); Heikki Lanckriet, Cambridge (GB)

(73) Assignee: Expedeon Limited, Babraham, Cambridge, Cambridgeshire (GB)

( * ) Notice: Subject to any disclaimer, the term of this patent is extended or adjusted under 35 U.S.C. 154(b) by 843 days.

(21) Appl. No.: 11/587,267

(22) PCT Filed: Apr. 25, 2005

(86) PCT No.: PCT/GB2005/050056
§ 371 (c)(1),
(2), (4) Date: Sep. 24, 2007

(87) PCT Pub. No.: WO2005/103068
PCT Pub. Date: Nov. 3, 2005

(65) Prior Publication Data
US 2008/0281085 A1   Nov. 13, 2008

(30) Foreign Application Priority Data

Apr. 23, 2004 (GB) .................................. 0409088.2
Mar. 15, 2005 (GB) .................................. 0505229.5

(51) Int. Cl.
*A61K 31/715* (2006.01)
(52) U.S. Cl. ........................................ 514/54; 530/402
(58) Field of Classification Search .................. 530/350, 530/402; 514/54
See application file for complete search history.

(56) References Cited

U.S. PATENT DOCUMENTS

| 4,758,515 A | 7/1988 | Bärwald et al. |
| 5,563,057 A | 10/1996 | Gellman et al. |
| 5,728,804 A | 3/1998 | Sharma et al. |
| 6,534,647 B1 * | 3/2003 | Stevens et al. ................. 536/115 |
| 6,569,999 B2 | 5/2003 | Machida et al. |
| 2003/0199066 A1 | 10/2003 | Machida et al. |
| 2004/0265291 A1 * | 12/2004 | Drake et al. ............... 424/93.45 |

FOREIGN PATENT DOCUMENTS

| GB | 2 405 872 A | 3/2005 |
| JP | 2002-155099 | 5/2002 |
| WO | WO 96/38468 A | 12/1996 |
| WO | WO 96/41870 A | 12/1996 |
| WO | WO 03/031043 A1 | 4/2003 |
| WO | WO 2005/026196 A | 3/2005 |

OTHER PUBLICATIONS

Hinrichs, W.L.J. et al., "Insulin glasses for the stabilization of therapeutic proteins," *International Journal of Pharmaceutics* Mar. 14, 2001; 215(1-2): 163-174.

Machida, A.S. et al., "Cycloamylose as an efficient artificial chaperone for protein refolding," *FEBS Letters* Dec. 8, 2000; 486(2): 131-135.

Sivakama, S.C. et al., "Artificial chaperoning of insulin, human carbonic anhydrase and hen egg lysozyme using linear dextrin chains-a sweet route to the native state of globular proteins," *FEBS Letters* Jan. 29, 1999; 443(2): 215-219.

Zardeneta, G. et al., "Cardiolipin liposomes sequester a reactivatable partially folded rhodanese intermediate," *European Journal of Biochemistry* 1992; 210(3): 831-837.

* cited by examiner

*Primary Examiner* — Chih-Min Kam
(74) *Attorney, Agent, or Firm* — Wolf, Greenfield & Sacks, P.C.

(57) ABSTRACT

The invention relates to methods for folding protein comprising providing an aqueous solution of a protein in non-native conformation and a linear or branched sugar polymer comprising three or more saccharide units, or a derivative thereof at a concentration suitable to permit folding of the protein and incubating the solution to permit folding of the protein.

21 Claims, 7 Drawing Sheets

METHODS AND KITS FOR FOLDING PROTEINS

TECHNICAL FIELD

Figure 1:
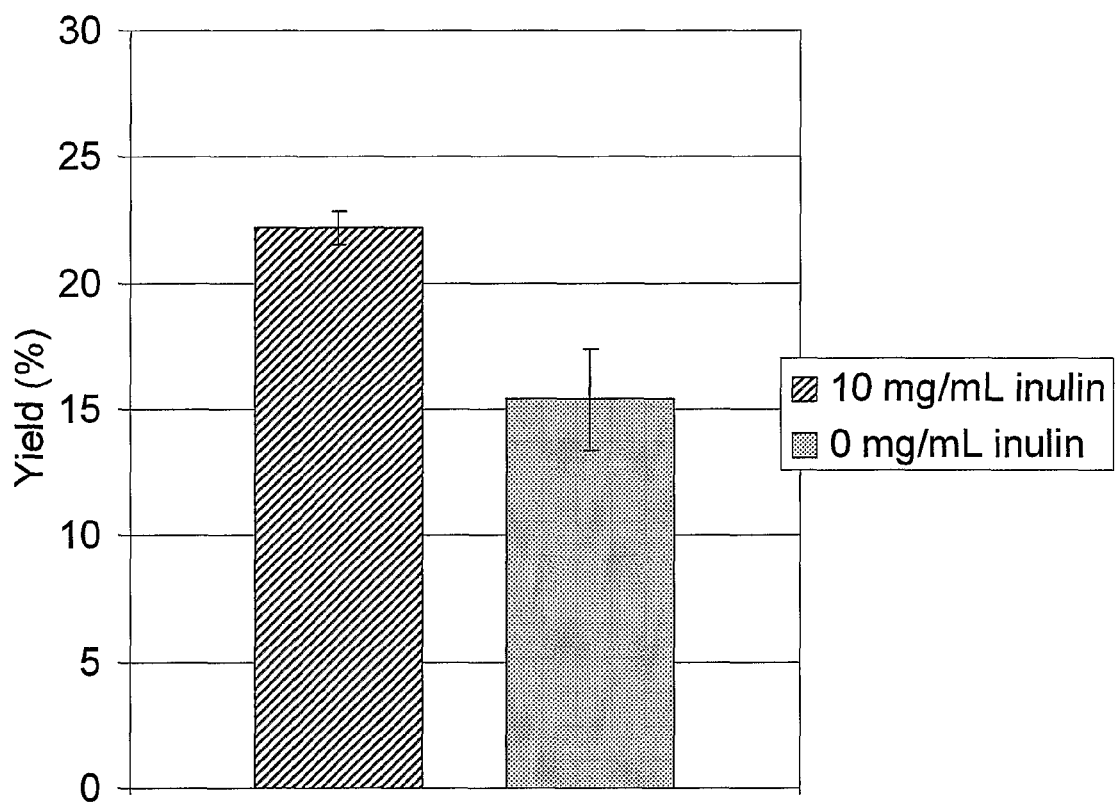

The present invention relates to methods, kits, consumables and reagents for controlling protein folding and aggregation.

BACKGROUND TO THE INVENTION

The biological function of a protein is dependent on its three dimensional structure. Proteins are formed as linear chains of amino acids, termed polypeptides. In vivo, in the appropriate conditions within the cell, the linear polypeptide chain is folded, a process which may be assisted by proteins called chaperones. A mature folded protein has an active three dimensional conformation known as the native structure. The structure depends on weak forces such as hydrogen bonding, electrostatic and hydrophobic interactions. These forces are affected by the protein's environment, so changes in the environment may cause structural disruption resulting in denaturation and/or degradation of the protein and loss of function. Such problems are encountered during processing of proteins and on storage of proteins.

The production of proteins by genetic engineering often results in the accumulation of non-active protein aggregates as inclusion bodies. After isolation and purification from the host cells, proteins or inclusion bodies have to be unfolded (denatured) and subsequently refolded (renatured) so that the proteins regain their native structure and bioactivity.

Traditional protein folding methods involve denaturant dilution or column-based approaches. Denatured protein is commonly refolded by diluting the denaturant. This induces a hydrophobic collapse of the protein molecule and in doing so the protein shields its hydrophobic patches in the core of the molecule. Unfortunately, on hydrophobic collapse, proteins do not always form the native bioactive conformation, two competing reactions occur: refolding and aggregation. It is suggested that a driver for protein aggregation is hydrophobic amino acid residues exposed at the surface of the molecule. Aggregation is undesirable and reduces the yield of functional, native protein. Refolding is known as a first order reaction (Rate=K*[prot]), but the aggregation reaction is favoured over refolding at high concentration as it is a higher order reaction (n) (Rate=K'*[prot]$^n$). The proportion of protein refolding:protein aggregation is strongly dependent on the protein concentration. At process scale this concentration dependency can result in increased aggregation, and thus reduced refolding yield. This can be due to imperfect mixing patterns in the protein solution. Processing large protein molecules is particularly difficult as they diffuse more slowly than the smaller denaturant molecules, thus creating micro-environments with high localised protein concentrations and low denaturant concentration, that is, an environment that favours protein aggregation over protein refolding.

For proteins with disulphide bonds the native protein often needs to be "matured"; during maturation, non-aggregated monomeric protein molecules with non-native disulphide bonds may be created initially; then, using a protein specific redox couple, the disulphide bonds shuffle and the protein matures to a functional protein molecule with native disulphide bonds.

Refolding processes usually involve dispersing the denatured protein molecules in a buffer in the presence of "refolding aids" to enhance renaturation. Folding aids usually increase the solubility of the folding intermediates and/or change the relative reaction rates of the folding and aggregation reactions. Polyethylene glycol and various sugars, e.g. sucrose, glucose, N-acetylglucosamine, and detergents, e.g. Chaps, Tween, SDS, Dodecylmaltoside have been employed as refolding aids (De Bernadez Clark (1998) Current Opinion Biotechnol. 9, 157-163).

$\alpha$, $\beta$ and $\gamma$ cyclodextrins (CDs) have been reported to be useful in stabilisation, solubilisation and affinity purification of certain enzymes, but both the nature of the interactions between these CDs and proteins, and their effect on bioactivity remain unclear. $\alpha$, $\beta$ and $\gamma$-cyclodextrins have been used as artificial chaperones to aid protein refolding in both detergent-free (Sharma et al, EP 0 871 651, U.S. Pat. No. 5,728,804) and detergent-containing refolding environments (Gellman & Rozema, U.S. Pat. No. 5,563,057). Cyclodextrins are cyclic oligosaccharides composed of multiple glucose residues. They are classified according to the number of sugar residues within the ring structure, $\alpha$-cyclodextrin has 6 glucose residues, $\alpha$-cyclodextrin has 7 glucose residues and $\gamma$-cyclodextrin has 8 glucose residues. Cyclodextrins can be modified by derivatisation to produce derivatives.

The inner cavity of cyclodextrins is hydrophobic whereas the outer surface is hydrophilic. The hydrophobic interior is capable of encapsulating poorly soluble drugs. The hydrophilic exterior assists in solubilisation, so cyclodextrins are useful adjuncts in pharmaceutical formulation.

EP 0 094 157 & U.S. Pat. No. 4,659,696 (Hirai et al) describe the use of $\alpha$-, $\beta$-, and $\gamma$-cyclodextrin derivatives in pharmaceutical compositions consisting essentially of a physical mixture of a hydrophilic, physiologically active (folded, native) peptide and a cyclodextrin derivative, the composition being a uniform mixture in dosage form.

EP 0 437 678 B1, U.S. Pat. Nos. 5,730,969 and 5,997,856 (Hora) describe methods for the solubilisation and/or stabilisation of polypeptides, especially proteins, using specified cyclodextrin derivatives: hydroxypropyl, hydroxyethyl, glucosyl, maltosyl, and maltotriosyl derivatives of $\beta$- and $\gamma$-cyclodextrin; the hydroxypropyl-$\beta$-cyclodextrin derivative being preferred. Also disclosed are aqueous and lyophilised compositions comprising a polypeptide, optionally a protein, and the above specified cyclodextrin derivatives.

EP 0 871 651 & U.S. Pat. No. 5,728,804 (Sharma et al) are concerned with a method for renaturing an unfolded or aggregated protein in a detergent-free aqueous medium with an amount of a cyclodextrin effective to renature said unfolded or aggregated protein. In this instance, the protein is present at a low concentration selected to minimise aggregation, preferably at around 0.05 mg/ml, and spontaneously refolds in a refolding buffer containing cyclodextrin. After refolding the cyclodextrin is removed by dialysis.

U.S. Pat. No. 5,563,057 (Gellman & Rozema) describes a method for refolding an enzyme from a misfolded configuration to a second native active configuration by adding a detergent having a linear alkyl non-polar portion, e.g. CTAB and Triton®-X 100 (Octoxynol-9), to misfolded enzyme to form an enzyme-detergent complex, which is then contacted with a cyclodextrin to allow the enzyme to assume the second active conformation.

Hinrichs et al (2001). International Journal of Pharmaceutics, 215, 163-174, describes the use of non-derivatised inulins, inulin SC 95 (DPn/DPw=5.5/6.0), inulin RS (DPn/DPw=14.2/19.4), and inulin EXL 608 (DPn/DPw 23.0/26.2) to protect alkaline phosphatase from degradation during freeze drying and subsequent storage of the dried protein.

WO 96/41870 (Gombac et al) describe frozen, dried or lyophilised hydrosoluble collagenase compositions containing isomalt and/or inulin (non-derivatised) to stabilise the collagenase.

To date, inulins have not been reported to be useful as protein folding aids. Inulins are D-fructans, generally consisting of chains of polyfructose in which the fructose units are connected to each other mostly or exclusively by .beta. (2-1) linkages. Inulin occurs in nature, in general, as a polydisperse mixture of polyfructose chains, most of which have a glucosyl unit at one terminus. Inulin can be obtained from bacterial syntheses, extracted from plants or can be made in vitro by enzymatic synthesis starting from sucrose. Inulin produced by bacteria is more branched than inulin from plant origin and commonly has a higher molecular weight (ranging from about 2,000 up to about 20,000,000), whereas inulin from plant origin is generally composed of linear or slightly branched polyfructose chains or mixtures thereof with a molecular weight commonly ranging from about 600 to about 20,000.

Inulin can be represented, depending from the terminal carbohydrate unit, by the general formulae GF.n or F.n, wherein G represents a glucosyl unit, F a fructosyl unit, and n is an integer representing the number of fructosyl units linked to each other in the carbohydrate chain. The number of saccharide units (fructose and glucose units) in one inulin molecule is referred to as the degree of polymerisation, represented by (DP). Often, the parameter (number) average degree of polymerisation, represented by (DP), is used too, which is the value corresponding to the total number of saccharide units (G and F units) in a given inulin composition divided by the total number of inulin molecules present in said inulin composition, without taking into account the possibly present monosaccharides glucose (G) and fructose (F), and the disaccharide sucrose (GF). The average degree of polymerisation (DP) can be determined, for example, by the method described by L. De Leenheer (Starch, 46 (5), 193-196, (1994), and Carbohydrates as Organic Raw Materials, Vol. III, 67-92, (1996)).

Inulin is commonly prepared from plant sources, mainly from roots of Chicory (*Cichorium intybus*) and from tubers of Jerusalem artichoke (*Helianthus tuberosus*), in which inulin can be present in concentrations of about 10 to 20% w/w of fresh plant material. Inulin from plant origin is usually a polydisperse mixture of linear and slightly branched polysaccharide chains with a degree of polymerisation (DP) ranging from 2 to about 100. In accordance with known techniques, inulin can be readily extracted from said plant parts, purified and optionally fractionated to remove impurities, mono- and disaccharides and undesired oligosaccharides, in order to provide various grades of inulin, e.g. as described in EP 0 769 026 and EP 0 670 850.

Inulin is commercially available, typically with a (DP) ranging from about 6 to about 40. Inulin from chicory is for example available as Inutec®N25 and RAFTILINE® from ORAFTI, (Tienen, Belgium) in various grades. Typical RAFTILINE® grades include RAFTILINE® ST (with a (DP) of about 10 and containing in total up to about 8% by weight glucose, fructose and sucrose), RAFTILINE® LS (with a (DP) of about 10 but containing in total less than 1% by weight glucose, fructose and sucrose), and RAFTILINE® .RTM HP (with a (DP) of at least 23, commonly with a (DP) of about 25, and virtually free of glucose, fructose and sucrose).

Inulins with a lower degree of polymerisation, usually defined as a (DP)<10, are commonly named inulo-oligosaccharides, fructo-oligosaccharides or oligofructose. Oligofructose can be obtained by partial (preferably enzymatic) hydrolysis of inulin and can also be obtained by enzymatic in vitro synthesis from sucrose according to techniques which are well-known in the art. Several grades of oligofructose are commercially available, for example as RAFTILOSE® from Orafti, (Tienen, Belgium), e.g. RAFTILOSE® P95 with a mean content of about 95% by weight of oligofructose with a degree of polymerisation (DP) ranging from 2 to 7 and containing about 5% by weight in total of glucose, fructose and sucrose. Inulins derivatised with hydrophobic alkyl chains on the polyfructose backbone are commercially available, for example Inutec® SP1 (SP1) from Orafti (Tienen, Belgium).

Various inulin derivatives and methods for the preparation of inulin derivatives are described in U.S. Pat. No. 6,534,647 (Stevens et al), the entire contents of which are incorporated herein by reference.

Starch is a well-known carbohydrate that is abundantly present in many plants as a biodegradable reserve polysaccharide. Starch molecules are polymers composed of D-glucosyl units which are linked to one another by $\alpha$-1,4 glucosyl-glucosyl bonds, thus forming a linear chain starch structure (termed amylose) or by $\alpha$-1,4 and $\alpha$-1,6 glucosyl bonds thus forming a branched chain starch structure (termed amylopectin) having a $\alpha$-1,6 glucosyl-glucosyl bond at the branching point. Starch occurs in nature as a polydisperse mixture of polymeric molecules which have, depending on the plant source, mainly a linear structure or mainly a branched structure. Starch can also occur in nature as a polydisperse mixture of molecules with said structures. The degree of polymerisation (DP), i.e. the number of glucosyl units linked to one another in a starch molecule, may widely vary and it depends largely on the plant source and the harvesting time.

The linkages between the glucosyl units are sensitive to hydrolysis, heat and shearing forces. This phenomenon is industrially exploited to prepare various starch derivatives, generically termed herein starch hydrolysates, through acidic hydrolysis, enzymatic hydrolysis, thermal treatment or shearing, or through combinations of said treatments. Depending on the source of the starch, the hydrolysis catalyst, the hydrolysis conditions, the thermal treatment and/or the shearing conditions, a wide variety of starch hydrolysates can be obtained, ranging from a product essentially composed of glucose, over products commonly termed glucose syrups, to products commonly termed maltodextrins and dextrins. Starch hydrolysates are well known in the art.

D-glucose (dextrose) presents strong reducing power. Starch hydrolysates are polydisperse mixtures, composed of D-glucose, oligomeric (DP<10) and/or polymeric (DP>10) molecules composed of D-glucosyl chains, which also present reducing power resulting from the presence of D-glucose and reducing sugar units (which are essentially terminal glucosyl units) on the oligomeric and polymeric molecules.

As a result, starting from a given starch product, the greater the extent of the hydrolysis, the more molecules (monomeric D-glucose, oligomeric and remaining polymeric molecules) will be present in the hydrolysate, and thus the higher the reducing powder of the starch hydrolysate obtained. Accordingly, the reducing power of starch hydrolysates has become the distinguishing feature of choice to differentiate and designate the various starch hydrolysate products. The reducing power is expressed as dextrose equivalents (D. E.) which formally corresponds to the grams of D-glucose (dextrose) per 100 grams of dry substance. D-glucose having by definition a D. E. of 100, the D. E. indicates the amount of D-glucose and reducing sugar units (expressed as dextrose) in a given product on a dry product basis. Thus the D. E. is in fact also a measurement of the extent of hydrolysis of the starch and also a relative indication of the average molecular weight of the glucose polymers in the starch hydrolysate.

The D. E. of starch hydrolysates, apart from hydrolysates composed essentially of D-glucose, may range from 1 to about 96 and starch hydrolysates are commercially available in a wide variety of grades based on the D. E.

Hydrolysates with a D. E. greater than 20 are commonly termed glucose syrups. Glucose syrups with a D. E. up to 47 can be dried by conventional techniques, for example by spray drying, to yield so-called "dried glucose syrups" in powder form, containing a maximum of about 5 wt % humidity.

Hydrolysates with a D. E. of 20 or less are commonly termed maltodextrins and dextrins. The manufacturing process usually involves a spray drying step at the end, yielding these hydrolysate products in powder form also containing a maximum of about 5 wt % humidity (wt % indicates % by weight).

Glucose syrups, maltodextrins and dextrins are made industrially at large scale from various starch sources under controlled hydrolysis conditions according to well-known methods. The various grades of starch hydrolysates obtained are usually defined by their starch source material and by their D. E. value, often in combination with an indication of the method of manufacture (e.g. maltodextrins/dextrins).

Although following certain Regulations the term "maltodextrins" is reserved to designate products derived from corn starch, the term maltodextrin(s) used herein is not limited to hydrolysates of corn starch, but indicates herein starch hydrolysates with a D. E. of 20 or less obtained from starch from any source.

Typical commercial sources of starch are corn, potato, tapioca, rice, sorgum and wheat. However, the starch hydrolysates suitable for use in connection with the present invention are not limited to starch from said sources, they extend to starch hydrolysates obtained from starch from any source.

Glucose syrups, maltodextrins and dextrins are well known and commercially available. For example, the production, properties and applications of glucose syrups and maltodextrins have been described in review articles in the book Starch Hydrolysis Products, Worldwide Technology, Production and Applications, Weinheim VCH Publishers Inc. (1992). Furthermore, in the technical brochure "GLUCIDEX Brochure 8/09.98" from the company Roquette, maltodextrins and dried glucose syrups are described and various grades are offered for sale.

There is a need for methods for the efficient preparation of correctly folded, non-aggregated, active protein, particularly for proteins produced using recombinant techniques. Control of folding and aggregation of proteins during processing and on storage is a recognised problem in many industries, in particular the pharmaceutical and biotechnology industries. The problems encountered with proteins may make manufacture of proteins difficult, result in low yields and render processes uneconomic, Methods, consumables, reagents and kits that permit control of protein refolding and modulate protein aggregation are commercially important. It is an object of the present invention to provide methods of protein folding, such that the disadvantages associated with present methods are alleviated.

Problems addressed by the present invention include reducing protein aggregation and achieving control of protein refolding, in particular of folding protein from a stable non-native state to a partially or fully folded state in a controlled manner to reduce aggregation and thereby increase the yield of soluble intermediates or native protein.

DISCLOSURE OF INVENTION

The present invention provides a method for folding protein comprising providing an aqueous solution of a protein in non-native conformation and a sugar polymer or sugar polymer derivative, said sugar polymer or sugar polymer derivative not being an α-, β- or γ-cyclodextrin or a derivative thereof, or a mixture of sugar polymer(s) and/or sugar polymer derivative(s), and incubating the solution to permit folding of the protein.

The present invention provides a method for folding protein comprising providing an aqueous solution of a protein in non-native conformation and one or more sugar polymer and/or sugar polymer derivative, said sugar polymer or sugar polymer derivative not being an α-, β- or γ-cyclodextrin; and incubating the solution to permit folding of the protein.

The present invention also provides a method for folding protein comprising providing an aqueous solution of a protein in non-native conformation and one or more sugar polymer(s) selected from linear or branched sugar polymer(s) comprising three or more saccharide units and derivative(s) thereof and incubating the solution to permit folding of the protein.

The sugar polymer or sugar polymer derivative is preferably a linear or branched sugar polymer derivative comprising 3 or more monosaccharide units. The terms "sugar polymer" and "sugar polymer derivative" as used herein exclude α-, β- and γ-cyclodextrin and derivatives thereof. One, or more (i.e. a mixture of), sugar polymers and/or sugar polymer derivative(s) may be employed in methods of the invention. Suitable sugar polymer derivatives are those which are capable of shielding hydrophobic amino acid side chains or modifying the net protein charge or hydrogen bonding characteristics. The term "sugar polymer derivative" as used herein encompasses polymeric and oligomeric saccharide molecules comprising three or more monosaccharide units in which one or more monosaccharide units per sugar polymer has been modified by derivatising a substituent present therein. The sugar polymer derivative can be a linear or non-linear (i.e. branched) amphipathic sugar polymer derivative.

Sugar polymer derivatives employed in methods of the invention may comprise one or more sugar(s) selected from the group consisting of: erythrose, threose, ribose, arabinose, xylose, lyxose, allose, altrose, glucose, mannose, gulose, idose, galactose, talose, psicose, fructose, sorbose, tagatose, xylulose and ribulose. Of these sugars, glucose, fructose, mannose and/or galactose, are the four most common simple (monomer) sugar units. The sugar polymer derivative can be a dextran, cellulose, amylose, starch, pullulan, mannan, chitin, chitosan, inulin, levan, xylan, cyclodextrin (provided that it is not an alpha, beta or gamma cyclodextrin or derivative thereof, cycloamylose or a derivative thereof. Suitable sugar polymer derivatives are disclosed in U.S. Pat. Nos. 5,202,433 and 5,204,457, the entire contents of which are incorporated herein by reference. Particularly preferred sugar polymers and derivatives for use in methods and kits of the invention are inulins and glucosides as described herein.

Amphipathic sugar polymers are capable of hydrophobic interaction with native and/or denatured protein. Derivatisation of the sugar polymer with appropriate substituents enhances the amphipathic nature and strength of interaction with the protein. Suitable substituents for sugar polymer derivatives used in the method of the invention include substituents selected from the group consisting of: alkyl groups having from 1 to 25 carbon atoms, alkenyl and alkynyl groups having from 2 to 25 carbon atoms, haloalkyl groups having from 1 to 25 carbon atoms, cycloalkyl groups having from 3 to 9 carbon atoms, aryl groups having from 6 to 14 carbon atoms, aralkyl groups comprising alkyl groups having from 1 to 25 carbon atoms which are substituted with 1 or more aryl groups having from 6 to 14 carbon atoms, fatty acids groups having from 2 to 25 carbon atoms and polyols having from 1 to 25 carbon atoms. One or more substituents per carbohydrate molecule can be present. The alkyl, alkenyl, alkynyl, haloalkyl, aralkyl, fatty acid and polyol groups may be straight chain or branched chain groups. Preferably, the substituents are selected from alkyl, alkenyl and alkynyl groups having from 2 to 25 carbon atoms, more preferably they are selected from alkyl, alkenyl and alkynyl groups having from 3 to 22 carbon atoms, and most preferably they are selected from alkyl, alkenyl and alkynyl groups having from 3 to 18 carbon atoms.

Incubation of the protein in non-native configuration with the sugar polymer or sugar polymer derivative, or mixture of sugar polymer(s) and/or sugar polymer derivative(s) at an appropriate concentration permits spontaneous folding of the protein.

The term "protein" as used herein encompasses proteins, peptides, polypeptides and oligopeptides. Proteins may be synthetic or naturally occurring, and may be obtained by chemical synthesis, or by recombinant or non-recombinant methods. The protein may be produced using DNA recombination or mutation techniques. The protein may be produced in vivo in a whole animal, or in a eukaryotic or prokaryotic cell; alternatively, the protein may be generated using an in vitro method such as cell-free in vitro translation e.g. using *E. coli* lysate, wheat germ extract, or rabbit reticulocyte. Cell free in vitro translation methods can be employed following in vitro transcription, e.g. following phage or ribosome display.

The protein in non-native conformation in aqueous solution is denatured and can be fully denatured, or partially denatured or partially renatured such that the protein is in non-native form as unfolded protein and/or partially folded refolding intermediate(s). An aqueous solution or dried sample comprising denatured protein may contain one or more of these forms. A native protein is in a folded, functional conformation. Some protein may also be present in aqueous solution, or in a dried sample, in the form of contaminating aggregates and/or inclusion bodies.

Protein folding encompasses both folding and refolding. The protein may fold to form a partially folded protein folding intermediate and/or a folded functional protein.

The concentration of the sugar polymer or sugar polymer derivative or mixture of sugar polymer(s) and/or sugar polymer derivative(s), used in methods for folding protein will depend on various factors such as the temperature, solution conditions and the protein itself. Suitable concentrations of the sugar polymer or sugar polymer derivative or mixture of sugar polymer(s) and/or sugar polymer derivative(s) for folding protein can be readily determined by those skilled in the art. In methods for folding protein, the sugar polymer or sugar polymer derivative or a mixture of sugar polymer(s) and/or sugar polymer derivative(s) is suitably present in the folding reaction solution at a low to medium concentration, e.g. at a concentration in the range of from 0.005 mg/ml to 50 mg/ml, or of from 0.002 mg/ml to 20 mg/ml, e.g. from 0.05 to 5 mg/ml, or 0.01 to 1 mg/ml.

Protein folding conditions (buffer, ionic strength, pH, temperature, redox potential) are highly protein specific. Methods according to the present invention enhance folding yield in a range of conditions previously known and may extend the range of conditions that support protein folding. The reaction conditions, protein concentration and the concentration of the one or more sugar polymer(s) and/or derivative(s) thereof are such that initially the protein is present in a non-aggregated non-native state, which may be a partially folded intermediate state and/or an unfolded state. A small amount, preferably less than 5% of the protein may be present in the form of contaminating aggregates and/or inclusion bodies.

In prior art methods, refolding has been carried out at low protein concentrations, (e.g. for lysozyme usually less than 0.10 mg/ml). However, methods, kits, reagents and consumables of the invention enable protein folding over a range of protein concentrations, at higher protein concentrations than traditional methods and with reduced aggregation. Protein concentrations at which methods of the invention can be performed are generally in the range of from 0.001 to 1.0 mg/ml, preferably in the range of 0.005 to 0.6 mg/ml, more preferably in the range of from 0.01 to 0.3 mg/ml. The protein concentration chosen will depend on factors such as the size of the protein. Although several smaller proteins have been successfully refolded at higher protein concentrations, often a lower protein concentration is needed for folding large proteins. The advantage of using high protein concentrations is reduced processing volume, resulting in easier purification, reduced reagent usage and reduced capital expenditure (smaller equipment size).

In protein folding methods of the invention, incubation is performed desirably at a temperature in the range of from about 0° C. to about 45° C., preferably from about 4° C. to about 42° C., further preferably from about 4° C. to about 37° C., yet further preferably from about 4° C. to about 30° C., more preferably from about 4° C. to about 25° C.

In certain embodiments of the method, multi-step incubation, e.g. a two step incubation is employed, such that after the initial incubation a further incubation is performed at a temperature that is higher than that of the first incubation, suitably in the range of from about 20° C. to about 45° C. In two step incubation methods, preferably the initial incubation is performed at about 4° C. and the further incubation is performed at room temperature (about 25° C.), about 37° C. or about 42° C.; alternatively the initial incubation can be performed at room temperature (about 25° C.) and the further incubation is then performed at about 30° C., about 37° C., about 42° C. or about 450°. By monitoring protein folding at a particular folding reaction incubation temperature, the optimum incubation period can be determined for specific proteins in the reaction conditions used.

The duration of an incubation step is typically 72 hours or less, preferably 48 hours or less, more preferably 24 hours or less, e.g. 1, 2, 4, 8, 12, or 15 hours, with overnight incubation of about 12 to 15 hours being generally convenient.

As used herein, removal means reduction of the concentration of the reagent being removed, and can be a partial removal, essentially complete or complete removal of the reagent from the reaction mixture.

In embodiments of the protein folding methods of the invention in which the sugar polymer(s) and/or derivative(s) are removed during and/or after the protein refolding incubation reaction, preferred removal methods are dilution, buffer exchange through dialysis, diafiltration, filtration, precipitation and/or a chromatographic method, suitable chromatographic methods include gel permeation, size exclusion chromatography, ion exchange chromatography, or affinity chromatography.

Alternatively or additionally, removal of the sugar polymer(s) and/or sugar polymer derivative(s) after protein folding can be by degradation of the sugar polymer(s) and/or sugar polymer derivative(s), suitably by one or more of the following methods: chemical degradation, enzymic degradation, electromagnetic radiation, shear stress or heat. Particularly preferred degradation methods involve removal of the sugar polymer(s) and/or derivative(s) by chemical and/or enzymic digestion, most preferably by enzymic digestion.

In embodiments in which the or a sugar polymer or derivative thereof is an inulin, enzymic digestion of the inulin can be performed using one or more exo-inulinase(s) and/or endo-inulinase(s), such as the exo-inulinase Fructan β-fructosidase E.C.3.2.1.80 and/or the endo-inulinase E.C.3.2.1.7

The EC numbers are Enzyme Commission numbers assigned by the IUPAC (International Union of Pure and Applied Chemistry) and IUBMB (international Union of Biochemistry and Molecular Biology) Joint Committee on Biochemical Nomenclature. Further information on the enzymes can be found in *Enzyme Nomenclature* 1992 [Academic Press, San Diego, Calif., ISBN 0-12-227164-5 (hardback), 0-12-227165-3 (paperback)] with Supplement 1 (1993), Supplement 2 (1994), Supplement 3 (1995), Supplement 4 (1997) and Supplement 5 (in *Eur. J. Biochem.* 1994, 223, 1-5; *Eur J. Biochem.* 1995, 232, 1-6; *Eur. J. Biochem.* 1996, 237, 1-5; *Eur. J. iochem.* 1997, 250; 1-6, and *Eur. J. Biochem.* 1999, 264, 610-650; respectively) [Copyright IUBMB]. A regularly updated web-based version of this publication is available at: chem.qmul.ac.uk/iubmb/enzyme/.

In embodiments in which the or a sugar polymer or derivative thereof is a glucoside or derivative thereof, e.g. a glucoside hydrocarbyl derivative as described herein, enzymic digestion can be performed using one or more amylase, cellulase and/or de-branching enzyme.

In folding methods of the invention, one or more of a chitin, chitosan, cyclodextrin, cyclodextrin derivative, cycloamylose, cycloamylose derivative, hydrophobic resin and/or hydrophobic gel can be included in the folding solution, and can be included at the start of the protein folding reaction, or included in the protein folding reaction during incubation, i.e. after an initial incubation period. Such methods may further comprise removal of the one or more of the chitin, chitosan, cyclodextrin, cyclodextrin derivative, cycloamylose, cycloamylose derivative, hydrophobic resin and/or hydrophobic gel from the solution, either during or after the folding reaction.

The terms "cyclodextrin" and "cyclodextrin(s)" as used herein include cyclodextrins such as α-cyclodextrin, a β-cyclodextrin, a γ-cyclodextrin and derivatives thereof (e.g. hydroxypropyl, hydroxyethyl, glucosyl, maltosyl, and maltotriosyl and methyl derivatives of β- and γ-cyclodextrin). One or more (i.e. a mixture of, cyclodextrin(s) may be used in certain methods of the invention.

Commercially available cycloamyloses and cycloamylose derivatives are suitable for use in protein folding methods of the invention and can be obtained, for example, from Sigma Aldrich. One or more cycloamylose(s), and/or cycloamylose derivative(s) may be used in protein folding methods of the invention.

Various chitins and chitosans are suitable for use in protein folding methods of the invention; chitins are commercially available for many sources, e.g. Sigma Aldrich. One or more chitin(s) and/or one or more chitosan(s) may be used in protein folding methods of the invention.

Suitable hydrophobic resins (beads) and gels for use in protein folding methods of the invention include those with a hydrophilic outer surface and a pore size sufficient to exclude the protein. The pore/core is hydrophobic and capable of binding molecules such as low molecular weight hydrophobic molecules to partially or essentially completely remove them. Commercially available sources include Bio-Beads SM Adsorbents (Bio-Rad) and Extractic-Gel D Detergent Removing Gel (Pierce, Perbio in UK).

The invention also provides protein folding methods as defined above in which a cyclodextrin, a cyclodextrin derivative or a mixture of cyclodextrin(s) and/or cyclodextrin derivative(s) is included in the protein folding solution. The cyclodextrin(s) is preferably introduced into the protein folding solution during the folding process, e.g. after an initial incubation period or periods. Protein folding methods of the invention may involve a multi-step incubation, e.g. a two step incubation, in which the protein is initially incubated with one or more sugar polymer(s) and/or sugar polymer derivative(s) (e.g. for 30 minutes, 1, 2, 4, 6, 8, 12 hours or overnight from about 12 to 15 hours), suitably at a temperature in the range of from about 0° C. to about 45° C., preferably from about 4° C. to about 42° C., further preferably from about 4° C. to about 37° C., yet further preferably from about 4° C. to about 30° C., more preferably from about 4° C. to about 25° C., with incubation at room temperature (about 25° C.) being appropriate for most proteins. Then, one or more cyclodextrin(s) and/or cyclodextrin derivative(s) can be introduced into the solution and the incubation continued (e.g. for 30 minutes, 1, 2, 4, 6, 8, 12 hours or overnight from about 12 to 15 hours), suitably with incubation being performed at a temperature in the range of from about 0° C. to about 45° C., preferably from about 4° C. to about 42° C., further preferably from about 4° C. to about 37° C., yet further preferably from about 4° C. to about 30° C., more preferably from about 4° C. to about 25° C., with an incubation temperature of 4° C. being appropriate for most proteins. In methods of the invention it is believed that the cyclodextrin will displace the sugar molecule from the protein and thus help the protein to refold. Such methods may further comprise removal of the cyclodextrin(s) and/or cyclodextrin derivative(s) from the solution. The cyclodextrin(s) can be removed from the solution during and/or after protein folding. Removal of the cyclodextrin(s) and/or cyclodextrin derivative(s) from the solution is preferably by degradation, e.g. by one or more of the following methods: chemical degradation, enzymic degradation, electromagnetic radiation, shear stress or heat. Chemical and/or enzymic degradation are preferred, with enzymic degradation being most preferable, e.g. using an amylase and/or glucosyl transferase, suitably one or more enzyme selected from the group comprising: cyclomaltodextrinase (Cdase, EC 3.2.1.54), Neopullulanase (Npase, EC 3.2.1.135) and maltogenicamylase (Mase, EC 3.2.1.133). Alternatively or additionally removal of the cyclodextrin(s) and/or derivative(s) thereof can be performed by precipitation, dilution, buffer exchange through dialysis, diafiltration, filtration and/or a chromatographic method (such as gel permeation, size exclusion chromatography, ion exchange chromatography, or affinity chromatography).

The invention also provides protein folding methods as defined above in which a cycloamylose, a cycloamylose derivative or a mixture of cycloamylose(s) and/or cycloamylose derivative(s) is included in the protein folding solution. The cycloamylose(s) is preferably introduced into the protein folding solution during the folding process, e.g. after an initial incubation period or periods. Protein folding methods of the invention may involve a multi-step incubation, e.g. a two step incubation, in which the protein is initially incubated with one or more sugar polymer(s) and/or sugar polymer derivative(s) (e.g. for 30 minutes, 1, 2, 4, 6, 8, 12 hours or overnight from about 12 to 15 hours), suitably at a temperature in the range of from about 0° C. to about 45° C., preferably from about 4° C. to about 42° C., further preferably from about 4° C. to about 37° C., yet further preferably from about 4° C. to about 30° C., more preferably from about 4° C. to about 25° C., with incubation at room temperature (about 25° C.) being appropriate for most proteins. Then, one or more cycloamylose(s) and/or cycloamylose derivative(s) can be introduced into the solution and the incubation continued (e.g. for 30 minutes, 1, 2, 4, 6, 8, 12 hours or overnight from about 12 to 15 hours), suitably with incubation being performed at a temperature in the range of from about 0° C. to about 45° C., preferably from about 4° C. to about 42° C., further preferably from about 4° C. to about 37° C., yet further preferably from about 4° C. to about 30° C., more preferably from about 4° C. to about 25° C., with an incubation temperature of 4° C. being appropriate for most proteins. In methods of the invention it is believed that the cycloamylose will displace the sugar molecule from the protein and thus help the protein to refold. Such methods may further comprise removal of the cycloamylose(s) and/or cycloamylose derivative(s) from the solution. The cycloamylose(s) can be removed from the solution during and/or after protein folding. Removal of the cycloamylose (s) and/or cycloamylose derivative(s) from the solution is preferably by degradation, e.g. by one or more of the following methods: chemical degradation, enzymic degradation, electromagnetic radiation, shear stress or heat. Chemical and/or enzymic degradation are preferred, with enzymic degradation being most preferable, e.g. using an amylase and/or glucosyl transferase. Alternatively or additionally removal of the cycloamylose(s) and/or derivative(s) thereof can be performed by precipitation, dilution, buffer exchange through dialysis, diafiltration, filtration and/or a chromatographic method (such as gel permeation, size exclusion chromatography, ion exchange chromatography, or affinity chromatography).

Also encompassed within protein folding methods of the invention are methods in which one or more chitin(s), chitin derivative(s), chitosan(s), and/or chitosan derivative(s) is included in the protein folding solution. The one or more chitin(s), chitin derivative(s), chitosan(s), and/or chitosan derivative(s) is preferably introduced into the protein folding solution during the folding process, e.g. after an initial incubation period or periods. Protein folding methods of the invention may involve a multi-step incubation, e.g. a two step incubation, in which the protein is initially incubated with one or more sugar polymer or sugar polymer derivative (e.g. for 30 minutes, 1, 2, 4, 6, 8, 12 hours or overnight from about 12 to 15 hours) suitably at a temperature in the range of from about 0° C. to about 45° C., preferably from about 4° C. to about 42° C., further preferably from about 4° C. to about 37° C., yet further preferably from about 4° C. to about 30° C., more preferably from about 4° C. to about 25° C. and then one or more chitin(s), chitin derivative(s), chitosan(s), and/or chitosan derivative(s) can be introduced into the solution and the incubation continued (e.g. for 30 minutes, 1, 2, 4, 6, 8, 12 hours or overnight from about 12 to 15 hours) suitably at a temperature in the range of from about 0° C. to about 45° C., preferably from about 4° C. to about 42° C., further preferably from about 4° C. to about 37° C., yet further preferably from about 4° C. to about 30° C., more preferably from about 4° C. to about 25° C. These methods may further comprise removal of the chitin(s), chitin derivative(s), chitosan(s) and/or chitosan derivative(s) from the solution; the one or more chitin(s), chitin derivative(s), chitosan(s) and/or chitosan derivative(s) can be removed from the solution during and/or after protein folding.

Removal of one or more of the chitin(s), chitin derivative (s), chitosan(s) and/or chitosan derivative(s) can be carried out by degradation, e.g. by one or more of the following methods: chemical degradation, enzymic degradation, electromagnetic radiation, shear stress or heat, but is preferably performed by chemical and/or enzymic degradation. Enzymic degradation may involve the use of one or more enzyme selected from the group comprising: chitinase (EC 3.2.1.14), Lysozyme (EC 3.2.1.17), chitosanase (EC 3.2.1.132) and β-N-acetylhexosaminidase (EC 3.2.1.52). Alternatively or additionally, removal of the chitin(s), chitin derivative(s), chitosan(s) and/or chitosan derivative(s) can be achieved by precipitation, dilution, buffer exchange through dialysis, diafiltration, filtration and/or a chromatographic method (such as gel permeation, size exclusion chromatography, ion exchange chromatography, or affinity chromatography).

Methods according to the present invention permit folding/refolding of denatured proteins in solution so that properly folded, native conformation protein in solution can be efficiently recovered. Methods of the invention can be applied to virtually any protein, especially after solubilisation and/or denaturation of insoluble protein aggregates, inclusion bodies, or abnormal soluble aggregates.

Accordingly, the present invention provides a method for refolding protein, wherein the method for folding protein in non-native configuration is preceded by a denaturation incubation performed by using a chaotrope, detergent and/or reducing agent to denature protein and/or dissolve aggregated proteins and/or inclusion bodies to provide an aqueous solution of protein in non-native conformation (fully or partially denatured protein).

Suitable chaotropes include one or more of guanidine hydrochloride and/or urea.

The reducing agent can be one or more of dithiothreithiol, dithioerythritol, beta-mercaptoethanol and Tris(2-carboxyethyl)phosphine hydrochloride (TCEP.HCl).

The detergent employed can be one or more of an anionic detergent (e.g. lauroyl sarcosine, SDS), a cationic detergent (e.g. cetyl trimethylammonium bromide (CTAB)), a non-ionic detergent (e.g. Triton X 100, Tween 60 (Sorbitan), dodecylmaltoside and/or a zwitterionic detergent (e.g. CHAPS).

Suitable conditions, concentrations and combinations of denaturants such as chaotropes, detergents and/or reducing agents for denaturing proteins are well known in the art. Typically denaturation can be performed overnight (12 to 15 hours) at 4° C., or for about 3 hours at 37° C.

After denaturation, the concentration of chaotrope, detergent and/or reducing agent can be reduced by dilution or buffer exchange through dialysis, diafiltration, filtration, and/or a chromatographic method or methods such as gel permeation, size exclusion, chromatography, ion exchange chromatography or affinity chromatography. The concentration of chaotrope, detergent and/or reducing agent can be reduced prior to, at the start of and/or during the method for folding protein. Ideally the concentration of chaotrope, detergent and/or reducing agent is reduced to a level that would permit the native conformation to exist in solution, e.g. typically below 2 M urea or below 1 M guanidine hydrochloride.

In protein folding methods of the invention, one or more disulphide shuffling agent(s) can be included in the folding solution. Suitable disulphide shuffling agents for use in methods of the invention include reduced and oxidised glutathione, cysteine, cysteine isomerases and disulphide isomerases preferably at a concentration in the range of from 10 μM to 10 mM. Disulphide isomerases are preferably used at a concentration of from 10 μM to 10 mM.

In preferred embodiments of the invention, the sugar polymer or sugar polymer derivative is an inulin or inulin derivative or a mixture of inulin(s) and/or inulin derivative(s).

The choice of the one or more inulin(s) and/or derivative(s) thereof for use in methods of the invention is limited by the solubility of the inulin or derivative thereof in the folding reaction conditions. Suitably the inulin or inulin derivative has a degree of polymerisation of from about 3 to 500, 3 to 250 or 3 to 100, preferably from 3 to 50, more preferably from 10 to 50, yet more preferably from 15 to 40, further preferably from 20 to 30, e.g. 20, 21, 22, 23, 24, 25, 26, 27, 28, 29, 30. It is preferred that inulin derivatives are derivatised by one or more type(s) of non-polar hydrocarbyl group, e.g. those selected from the group comprising a linear alkyl derivative (s), branched alkyl derivative(s) or a mixture of linear alkyl derivative(s) and branched alkyl derivative(s). An inulin derivative suitable for use in methods of the invention is Inutec® SP1 (Orafti, Belgium).

A preferred inulin or inulin derivative for use in a method, use or kit of the invention is a compound of formula (I):

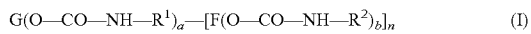
$$G(O\text{---}CO\text{---}NH\text{---}R^1)_a\text{---}[F(O\text{---}CO\text{---}NH\text{---}R^2)_b]_n \quad (I)$$

wherein:
G is a terminal glucosyl unit in which one or more hydroxyl groups thereof may be substituted with a group or groups of formula (O—CO—NH—$R^1$);
$R^1$ is selected from the group comprising alkyl groups, alkenyl groups, alkynyl groups, haloalkyl groups, cycloalkyl groups, aryl groups and aralkyl groups and, where there is more than one (O—CO—NH—$R^1$) group on the glucosyl unit, each $R^1$ group may be the same or different;
a is an integer of from 0 to 4;
F is a fructosyl unit in which one or more hydroxyl groups thereof may be substituted with a group or groups of formula (O—CO—NH—$R^2$);
$R^2$ is selected from the group comprising alkyl groups, alkenyl groups, alkynyl groups, haloalkyl groups, cycloalkyl groups, aryl groups and aralkyl groups and, where there is more than one (O—CO—NH—$R^1$) group on the glucosyl unit, each $R^1$ group may be the same or different and, where there is more than one (O—CO—NH—$R^2$) group on the fructosyl unit, each $R^2$ group may be the same or different;
b is an integer of from 0 to 3 and from 0 to 4 for the terminal fructosyl unit;
n is an integer of from 2 to 499 preferably of from 2 to 249, more preferably 2 to 99, yet more preferably 2 to 49, further preferably 9 to 49, yet further preferably 14 to 39, most preferably 19-24;
each unit of formula F(O—CO—NH—$R^2$)$_b$ may be the same or different from any other unit of formula F(O—CO—NH—$R^2$)$_b$; and
the average degree of substitution per glucosyl or fructosyl unit is from 0.01 to 3.0.

Where $R^1$ or $R^2$ is an alkyl group, it is a linear or branched chain alkyl group having from 1 to 25 carbon atoms; preferably, it has from 3 to 22 carbon atoms, and most preferably from 3 to 18 carbon atoms.

Where $R^1$ or $R^2$ is an alkenyl group, it is a linear or branched chain alkenyl group having from 2 to 25 carbon atoms; preferably, it has from 3 to 22 carbon atoms, and most preferably from 3 to 18 carbon atoms.

Where $R^1$ or $R^2$ is an alkynyl group, it is a linear or branched chain alkynyl group having from 2 to 25 carbon atoms; preferably, it has from 3 to 22 carbon atoms, and most preferably from 3 to 18 carbon atoms.

Where $R^1$ or $R^2$ is a haloalkyl group, it is an alkyl group as defined above which is substituted with 1 or more halogen atoms (e.g. fluorine, chlorine or bromine atoms). Preferably, said haloalkyl groups have from 1 to 3 halogen atom substituents, more preferably from 1 to 3 fluorine or chlorine atom substituents. Preferably, said haloalkyl groups have from 3 to 22 carbon atoms, and most preferably from 3 to 18 carbon atoms.

Where $R^1$ or $R^2$ is a cycloalkyl group, it is a cyclic alkyl group having from 3 to 9 carbon atoms; preferably, said cycloalkyl groups have from 3 to 7 carbon atoms and most preferably from 4 to 6 carbon atoms.

Where $R^1$ or $R^2$ is an aryl group, it is an aromatic group having from 6 to 14 carbon atoms in one or more rings, e.g. a phenyl group or a naphthyl group.

Where $R^1$ or $R^2$ is an aralkyl group, it is an alkyl group as defined above that is substituted with one or more aromatic groups having from 6 to 14 carbon atoms in one or more rings, e.g. a benzyl group or a triphenylmethyl group.

Each group $R^1$ and $R^2$ may be selected from alkyl groups having from 1 to 25 carbon atoms, and alkenyl and alkynyl groups having from 2 to 25, preferably 3 to 22, most preferably 3 to 18 carbon atoms. One or more of the groups $R^1$ and $R^2$ can be an alkyl group having from 1 to 25, preferably 3 to 22, most preferably 3 to 18 carbon atoms; suitably one or more of groups $R^1$ and $R^2$ is an alkenyl or alkynyl group having from 2 to 25, preferably 3 to 22, most preferably 3 to 18 carbon atoms. Each alkyl group $R^1$ and $R^2$ can be a linear alkyl group having from 1 to 25, preferably 3 to 22, most preferably 3 to 18 carbons or branched alkyl group having from 3 to 25, preferably 3 to 22, most preferably 3 to 18 carbons.

The average degree of substitution per glucosyl or fructosyl unit is suitably in a range of from 0.01 to 3.0, e.g. in the range of from 0.01 to 2.0, 0.02 to 3.0, 0.02 to 1.0, 0.05 to 1.0, 0.05 to 0.5, or 0.03 to 0.3.

The compound of formula (I) can be a polydisperse linear or slightly branched inulin N-alkylurethane, e.g. selected from the group consisting of inulin N-n-octyl-carbamates, inulin N-n-dodecylcarbamates and inulin N-n-octadecylcarbamates.

Other sugar polymer derivatives suitable for use in methods, uses and kits of the invention include hydrocarbyl urethane derivatives, e.g. glucoside hydrocarbyl derivatives of formula (II):

$$[G(O\text{---}CO\text{---}NH\text{---}R^1)_a]_n \quad (1)$$

wherein:
G is a glucosyl unit in which one or more hydroxyl groups thereof may be substituted with a group or groups of formula (O—CO—NH—$R^1$);
$R^1$ is a hydrocarbyl group selected from the group consisting of alkyl groups, alkenyl groups, alkynyl groups, haloalkyl groups, cycloalkyl groups, aryl groups and aralkyl groups and, where there is more than one (O—CO—NH—$R^1$) group on each glucosyl unit, each $R^1$ group may be the same or different;
a is an integer of from 0 to 4 for a terminal glucosyl unit, 0 to 3 for a non-branched, non-terminal glucosyl unit and 0 to 2 for a branched, non-terminal glucosyl unit;
n is an integer of from 3 to 499 preferably of from 3 to 249, 3 to 99, 3 to 49, 9 to 49, 14 to 39, 19 to 29, or 19 to 24,
each unit of formula G(O—CO—NH—$R^1$)$_a$ may be the same or different from any other unit of formula G(O—CO—NH—$R^1$)$_a$; and
the average degree of substitution per glucosyl unit is from 0.01 to 2.0, Where $R^1$ is an alkyl group, it is a linear or branched chain alkyl group having from 1 to 25 carbon atoms; preferably, it has from 3 to 22 carbon atoms, and most preferably from 3 to 18 carbon atoms.

Where $R^1$ is an alkenyl group, it is a linear or branched chain alkenyl group having from 2 to 25 carbon atoms; preferably, it has from 3 to 22 carbon atoms, and most preferably from 3 to 18 carbon atoms.

Where $R^1$ is an alkynyl group, it is a linear or branched chain alkynyl group having from 2 to 25 carbon atoms; preferably, it has from 3 to 22 carbon atoms, and most preferably from 3 to 18 carbon atoms.

Where $R^1$ is a haloalkyl group, it is an alkyl group as defined above which is substituted with 1 or more halogen atoms (e.g. fluorine, chlorine or bromine atoms). Preferably, said haloalkyl groups have from 1 to 3 halogen atom substituents, more preferably from 1 to 3 fluorine or chlorine atom substituents. Preferably, said haloalkyl groups have from 3 to 22 carbon atoms, and most preferably from 3 to 18 carbon atoms.

Where $R^1$ is a cycloalkyl group, it is a cyclic alkyl group having from 3 to 9 carbon atoms; preferably, said cycloalkyl groups have from 3 to 7 carbon atoms and most preferably from 4 to 6 carbon atoms.

Where $R^1$ is an aryl group, it is an aromatic group having from 6 to 14 carbon atoms in one or more rings, e.g. a phenyl group or a naphthyl group.

Where $R^1$ is an aralkyl group, it is an alkyl group as defined above that is substituted with one or more aromatic groups having from 6 to 14 carbon atoms in one or more rings, e.g. a benzyl group or a triphenylmethyl group.

Preferably, one or more of the groups $R^1$ can be a linear or branched chain alkyl group having from 1 to 25, preferably 3 to 22, most preferably 3 to 18 carbon atoms and/or one or more of groups $R^1$ can be an alkenyl or alkynyl group having from 2 to 25, preferably 3 to 22, most preferably 3 to 18 carbon atoms. Suitably each alkyl group $R^1$ is a linear alkyl group having from 1 to 25, preferably 3 to 22, most preferably 3 to 18 carbons or a branched alkyl group having from 3 to 25, preferably 3 to 22, most preferably 3 to 18 carbons.

In a compound of formula (II), the average degree of substitution per glucosyl unit is from 0.01 to 2.0, preferably from 0.02 to 1.0, and most preferably from 0.03 to 0.3.

The compound of formula (II) can be a polydisperse linear or branched glucoside N-hydrocarbyl urethane. Each glucosyl unit G may be a D-glucosyl or L-glucosyl unit, preferably a D-glucosyl unit. The glucosyl units can be linked via 1,4-linkages or 1,6-linkages, and each linkage can be an α-linkage or a β-linkage.

In preferred embodiments of the methods and uses of the present invention, said compounds of formula (II) are hydrocarbyl urethanes of starch hydrolysates.

Particularly preferred hydrocarbyl urethanes of starch hydrolysates are glucoside hydrocarbyl derivatives of formula (IIa) composed of units of formula (III):

$$G'(O\text{—}CO\text{—}NH\text{—}R^1)_b \quad (III)$$

wherein

G' represents a glucosyl unit of a starch hydrolysate molecule, the starch hydrolysate having a Dextrose Equivalent (D. E.) ranging from 1 to 47, $R^1$ is a hydrocarbyl group as defined above, and b represents the number of hydrocarbyl carbamate groups per glucosyl unit, which number is commonly expressed as the degree of substitution (DS), i.e. the average number of hydrocarbyl substituents per glucosyl unit of the glucoside hydrocarbyl urethane of formula (IIa), with said DS value ranging from 0.01 to 2.0.

The number of hydroxyl groups per glucosyl unit of the subject glucoside molecules which theoretically can be substituted by a carbamate group is, for a non-terminal, non-branched glucosyl unit, a maximum of 3, whereas the number for a terminal or for a non-terminal branched glucosyl unit is, respectively, 4 or 2. Furthermore, since the DS represents an average number of substituents per glucosyl unit, it is evident that in a glucoside N-hydrocarbyl carbamate (IIa) molecule there may be glucosyl units present which are not substituted by a hydrocarbyl carbamate group (thus b in formula (III) being zero for said glucosyl unit).

Starch hydrolysates commonly appear in the form of a polydisperse mixture of glucoside molecules. Accordingly, when such a mixture is used, as is usually the case, as starting material for the preparation of a glucoside hydrocarbyl urethane (IIa), the product obtained is also a corresponding polydisperse mixture of glucoside hydrocarbyl urethanes (IIa). Such polydisperse mixtures constitute a preferred embodiment of the glucoside hydrocarbyl urethanes (IIa) for utilisation in the methods and uses of the present invention.

Commercial grades of starch hydrolysates, composed of said polydisperse mixture of glucoside molecules and having a D. E. ranging from 1 to 47 are very suitable for the preparation of glucoside hydrocarbyl urethanes (IIa).

Typically suitable starch hydrolysates for use in the preparation of glucoside N-hydrocarbyl urethanes (IIa) of the invention are for example GLUCIDEX® maltodextrins and GLUCIDEX® dried glucose syrups which are available from ROQUETTE company, such as the maltodextrins of type I (potato based with D. E. max 5), type 2 (Waxy Maize based with D. E. max 5), type 6 (Waxy Maize based with D. E. 5 to 8), type 9 (Potato based with D. E. 8 to 10), and maltodextrins of type 12 (D. E. 11 to 14), type 17 (D. E. 15 to 18) and type 19 (D. E. 18 to 20), as well as dried glucose syrups of type 21 (D. E. 20 to 23), type 28E (D. E. 28 to 31), type 29 (D. E. 28 to 31), type 32 (D. E. 31 to 34), type 33 (D. E. 31 to 34), type 38 (D. E. 36 to 40), type 39 (D. E. 38 to 41), type 40 (D. E. 38 to 42) and type 47 (D. E. 43 to 47).

The hydrocarbyl group of the hydrocarbyl urethanes (IIa) of the present invention, i.e. the $R^1$ group in formula (III) defined herein above, is preferably a saturated $C_3\text{-}C_{22}$ alkyl group, more preferably a saturated $C_4\text{-}C_{18}$ alkyl group, even more preferably a saturated linear $C_4\text{-}C_{18}$ alkyl group, most preferably a saturated linear $C_6\text{-}C_{18}$ alkyl group. Typically suitable alkyl groups include butyl, hexyl, octyl, decyl, dodecyl, tetradecyl, hexadecyl and octadecyl groups.

In another preferred embodiment, the hydrocarbyl group is a $C_3\text{-}C_{22}$ alkenyl group, preferably a $C_4\text{-}C_{18}$ alkenyl group, most preferably a linear $C_5\text{-}C_{18}$ alkenyl group.

Typically suitable alkenyl groups include butenyl, hexenyl, octenyl, decenyl, dodecenyl, tetradecenyl, hexadecenyl and octadecenyl groups.

In the urethane (IIa) of the invention, all $R^1$ groups of the units of formula (III) may be the same or different. The latter urethanes (IIa) can be easily prepared, according to the method described below, by reacting a starch hydrolysate with an isocyanate of formula $R^1$—NCO which is in fact a mixture of two or more isocyanates bearing different $R^1$ groups defined above.

Saturated alkyl isocyanates can be prepared conventionally, e.g. by reacting a primary or secondary alkyl-amine with phosgene. Unsaturated alkylisocyanates can be prepared similarly from alkenyl-amines. α,β-unsaturated alkylisocyanates of formula $R^2R^3C\!\!=\!\!CH\text{—}NCO$ (IV) wherein the radical $R^2R^3C\!\!=\!\!CH\text{—}$ corresponds to the group $R^1$ of formula (III) and wherein $R^2$ represents hydrogen or an alkyl group and $R^3$ represents an alkyl or vinyl group, can be prepared by condensation of the aldehyde $R^2R^3CH\text{—}CHO$ with $Me_3C\text{—}NH2$, followed by reaction of the resultant Schiff base (in equilibrium with its enamine form) with phosgene, and thermal elimination of $Me_3C\text{—}Cl$ as disclosed by K. Koenig et al. (Angew. Chem., 21 (4), 334-335 (1979)). Furthermore, various unsaturated alkylisocyanates are disclosed, inter alia in U.S. Pat. No.

3,890,383 and U.S. Pat. No. 3,803,062 of Dow Chemical Co. Many alkyl cyanates of formula $R^1$—N=C—O ($R^1$ as defined above) are commercially available.

Glucoside hydrocarbyl urethanes (IIa) in accordance with the present invention have a degree of substitution (DS) per glucosyl unit of formula (III) ranging from 0.01 to 2.0, preferably from 0.02 to 1.0, and most preferably from 0.03 to 0.3.

The hydrocarbyl carbamate substituent or substituents can be located at various positions on the glucosyl units of the glucoside hydrocarbyl urethanes (IIa).

The glucoside hydrocarbyl urethanes (IIa) of the present invention can be prepared in analogy with conventional methods for the preparation of urethanes of monosaccharides, disaccharides, and polysaccharides, for example, by reacting the starch hydrolysate with the selected hydrocarbyl isocyanate or mixture of hydrocarbyl isocyanates, in solution in a solvent which is inert with respect to the starch hydrolysate, the isocyanate and the reaction product.

Suitable solvents include solvents or solvent mixtures which are free of reactive hydroxyl and amine groups, such as for example dimethyl formamide (DMF), dimethyl sulfoxide (DMSO) and N-methylpyrrolidone (NMP).

The reaction between the starch hydrolysate and the hydrocarbylisocyanate is preferably performed under anhydrous conditions. In view of this, the starch hydrolysate as well as the solvent(s) are dried, preferably to a water content of less than 0.5 wt %, prior to bringing them into contact with the hydrocarbyl isocyanate. Drying can be carried out by conventional techniques, including, for example by heating the starch hydrolysate in a stream of dry air, or by heating the starch hydrolysate under reduced pressure, or by removing the water through azeotropic distillation, optionally under reduced pressure, from a solution of the starch hydrolysate in the solvent chosen for the reaction. During drying a maximum temperature, depending on the nature of the starch hydrolysate and the solvent, should not be exceeded in order to avoid any decomposition or side reaction. Preferably said temperature should be kept below about 80° C.

The reaction is typically carried out by bringing the starch hydrolysate dissolved in a suitable solvent into contact, under gentle to vigorous stirring, with the hydrocarbyl isocyanate in neat form or dissolved in an anhydrous solvent. The reaction can be carried out over a wide temperature range, typically from room temperature up to about 80° C., or the reflux temperature of the reaction mixture if it is lower, preferably at a temperature between about 60° C. and about 80° C.

Typically, the starch hydrolysate is dissolved in a suitable solvent, where necessary under heating. Accordingly, the hydrocarbyl isocyanate (optionally dissolved in the same or in another inert solvent, but which is preferably miscible with the former solvent) is added slowly under stirring to the dissolved glucoside. The desired degree of substitution of the glucoside hydrocarbyl urethane (IIa) can be obtained by controlling the ratio of the reactants. Since the reaction of an hydrocarbyl isocyanate with an alcoholic hydroxyl group to form an urethane is a quantitative reaction, the degree of substitution of the urethane (IIa) can be controlled by the selection of the proper molar ratio of the hydrocarbyl isocyanate per glucosyl unit of the starch hydrolysate. Usually the reaction mixture is heated with stirring for a time period, usually from about 30 minutes to about 24 hours, in order to complete the reaction between the reagents. The reaction mixture is then worked up by conventional techniques, for example, by precipitating the formed urethane (IIa) through pouring the reaction mixture, usually after cooling to room temperature, in a precipitant solvent, which is a solvent that is miscible with the solvent or solvents used to dissolve the reagents but in which the glucoside alkyl urethane (IIa) is not or very poorly soluble. The urethane (IIa) is then physically isolated from the reaction mixture, for example by filtration or centrifugation, washed with a suitable solvent in which the urethane (IIa) is not or only very slightly soluble, and dried using any common technique.

A further convenient method to synthesise a desired urethane (IIa) according to the present invention, can be performed in an analogous manner to the one described by W. Gerhardt, Abh. Dtsch. Akad. Wiss. Berlin, KL. Chem. Geol. Biol., Vol 1966 (6), 24-36, (1967) (C. A., 6S, 14323). It involves the transformation in a one-pot reaction in dimethyl formamide of the starch hydrolysate with potassium cyanate and with a selected hydrocarbyl halogenide, preferably an hydrocarbyl bromide.

Preferably, the present invention provides a method for folding protein comprising providing an aqueous solution of a protein in non-native conformation and a glucoside hydrocarbyl derivative of formula (II) as defined above, and incubating the solution to permit folding of the protein. More preferably, the glucoside hydrocarbyl derivative of formula (II) is a hydrocarbyl urethane of a starch hydrolysate, particularly preferably a glucoside hydrocarbyl derivative of formula (IIa) composed of units of formula (III) as defined above.

The invention further provides novel kits and consumables suitable for use in folding methods of the invention, optionally together with instructions for use of the kit. Typically a kit will comprise one or more inulin(s) and/or inulin derivative(s), suitably of formula (I) and/or one or more glucoside hydrocarbyl derivative(s), suitably of formula (II). The kit may include in a container or containers, one or more inulin (s) and/or inulin derivative(s), suitably of formula (I) and/or one or more glucoside hydrocarbyl derivative(s), suitably of formula (II).

A kit for performing a folding method of the invention may comprise one or more inulin(s) and/or inulin derivative(s), suitably of formula (I), in a first container or containers and a substance or substances capable of degrading the inulin(s) and/or inulin derivative(s) (e.g. an enzyme or enzymes, such as exo-inulinase(s) and/or endo-inulinase(s)), in a second container or containers, optionally together with instructions for use of the kit.

A kit for performing a folding method of the invention may comprise one or more glucoside hydrocarbyl derivative(s), suitably of formula (II), in a first container or containers and a substance or substances capable of degrading the one or more glucoside hydrocarbyl derivative(s), (e.g. an enzyme or enzymes, such as an amylase, cellulase and/or debranching enzyme, in a second container or containers, optionally together with instructions for use of the kit.

The invention also provides consumables suitable for use in methods of the invention.

Thus the invention provides a support, such as a pipette tip, centrifuge tube, resin, gel, beads, membrane or column to which is attached a substance or substances capable of degrading an inulin and/or inulin derivative (e.g. an enzyme or enzymes, such as exo-inulinase(s) and/or endo-inulinase (s)) or glucoside hydrocarbyl derivative of formula (II) (e.g. an enzyme or enzymes, such as an amylase, cellulase and/or de-branching enzyme).

The invention further provides s support means, such as a pipette tip or centrifuge tube or column, containing a support to which is attached a substance or substances capable of degrading an inulin and/or inulin derivative or glucoside hydrocarbyl derivative of formula (II).

Also provided is a support means, such as a pipette tip or centrifuge tube or column, containing a support to which is attached an enzyme or enzymes capable of degrading an inulin and/or inulin derivative (e.g. one or more immobilised exo-inulinase(s) and/or endo-inulinase(s)), or to which is attached an enzyme or enzymes capable of degrading a glucoside hydrocarbyl derivative of formula (II). For example, a support means, such as a pipette tip or centrifuge tube or column, containing one or more immobilised exo-inulinase(s) and/or endo-inulinase(s) or one or more immobilised amylase, cellulase and/or de-branching enzyme.

Attachment, i.e. immobilisation of an enzyme on the support means and/or support is preferably through covalent bonding. e.g. via the amine, thiol, carboxylic acid or aldehyde functional groups of the enzyme.

A kit according to the invention may therefore comprise one or more inulin(s) and/or inulin derivative(s) in a container or containers and a support means such as a pipette tip, centrifuge tube, or column containing a support, such as a resin, gel, beads, or membrane to which is attached a substance or substances capable of degrading the one or more inulin(s) and/or inulin derivative(s).

A kit according to the invention may comprise one or more one or more inulin(s) and/or inulin derivative(s) in a container or containers, and a support, such as a pipette tip, centrifuge tube, resin, gel, beads, membrane, or column, to which is attached a substance or substances capable of degrading the one or more one or more inulin(s) and/or inulin derivative(s).

A kit according to the invention may comprise one or more inulin(s) and/or inulin derivative(s) in a container or containers, and a support means, such as a pipette tip, centrifuge tube, or column, containing a support, such as a resin, gel, beads or membrane to which is attached an enzyme or enzymes capable of degrading an inulin and/or inulin derivative (e.g. one or more endo-inulinase(s) and/or exo-inulinase(s)).

A kit according to the invention may comprise one or more glucoside hydrocarbyl derivative(s), suitably of formula (II), in a container or containers and a support means such as a pipette tip, centrifuge tube, or column containing a support, such as a resin, gel, beads, or membrane to which is attached a substance or substances capable of degrading the one or more one or more glucoside hydrocarbyl derivative(s).

A kit according to the invention may comprise one or more glucoside hydrocarbyl derivative(s), suitably of formula (II), in a container or containers, and a support, such as a pipette tip, centrifuge tube, resin, gel, beads, membrane, or column, to which is attached a substance or substances capable of degrading the one or more one or more one or more glucoside hydrocarbyl derivative(s).

A kit according to the invention may comprise one or more one or more glucoside hydrocarbyl derivative(s), suitably of formula (II), in a container or containers, and a support means, such as a pipette tip, centrifuge tube, or column, containing a support, such as a resin, gel, beads or membrane to which is attached an enzyme or enzymes capable of degrading one or more glucoside hydrocarbyl derivative(s).

Also provided is a kit comprising one or more glucoside hydrocarbyl derivative(s), suitably of formula (II), in a container or containers, and a support, such as a pipette tip, centrifuge tube, resin, gel, beads, membrane, or column, to which is attached one or more enzyme or enzymes capable of degrading one or more glucoside hydrocarbyl derivative(s).

A kit according to the invention may further comprise a substance or substances, preferably an enzyme or enzymes, capable of degrading a cyclodextrin and/or a cyclodextrin derivative.

A kit according to the invention may further comprise one or more of a, a chitin, chitin derivative, a chitosan, a chitosan derivative, a hydrophobic resin and/or a hydrophobic gel, and may comprise a substance or substances, preferably an enzyme or enzymes, capable of degrading a chitin, chitin derivative, a chitosan, and/or a chitosan derivative.

In methods, consumables and kits of the invention, degradation of the one or more inulin(s) and/or inulin derivative(s), or glucoside hydrocarbyl derivative(s) of formula (I) as defined above in the protein solution can be achieved by contacting the solution with, or passing the solution through a pipette tip, tube or column containing a substance or substances capable of degrading the inulin(s), inulin derivative(s) or glucoside hydrocarbyl derivative(s) of formula (II).

In methods, consumables and kits of the invention, degradation of the one or more inulin(s) and/or inulin derivative(s) in the protein solution can be achieved by contacting the solution with, or passing the solution through a pipette tip, tube or column containing a substance or substances capable of degrading the inulin and/or inulin derivative.

In methods, consumables and kits of the invention, degradation of the one or more glucoside hydrocarbyl derivative(s) in the protein solution can be achieved by contacting the solution with, or passing the solution through a pipette tip, tube or column containing a substance or substances capable of degrading the glucoside hydrocarbyl derivative(s).

The substance(s) may be directly immobilised on the tip, tube or column. Alternatively the pipette tip, tube or column may contain the substance(s) immobilised on a resin, gel, bead, membrane or other suitable supporting structure. Degradation of the one or more inulin(s) or inulin derivative(s) in the protein solution may also be achieved by contacting the solution with a resin, gel, bead, membrane, or other suitable supporting structure, to which is attached a substance or substances capable of degrading the one or more inulin(s) and/or inulin derivative(s). Degradation of the one or more glucoside hydrocarbyl derivative(s) in the protein solution may also be achieved by contacting the solution with a resin, gel, bead, membrane, or other suitable supporting structure, to which is attached a substance or substances capable of degrading the one or more glucoside hydrocarbyl derivative(s).

The kit may also contain buffers and other reagents suitable for use in performing a method of the invention.

LIST OF FIGURES

FIG. 1: Refolding yields for lysozyme (0.25 mg/ml final concentration) after 20 fold dilution into refolding buffer containing inulin. Inulin concentrations are shown in the legend. The samples were incubated for 24 hours at room temperature before the refolding measurements were taken.

Figure 2:
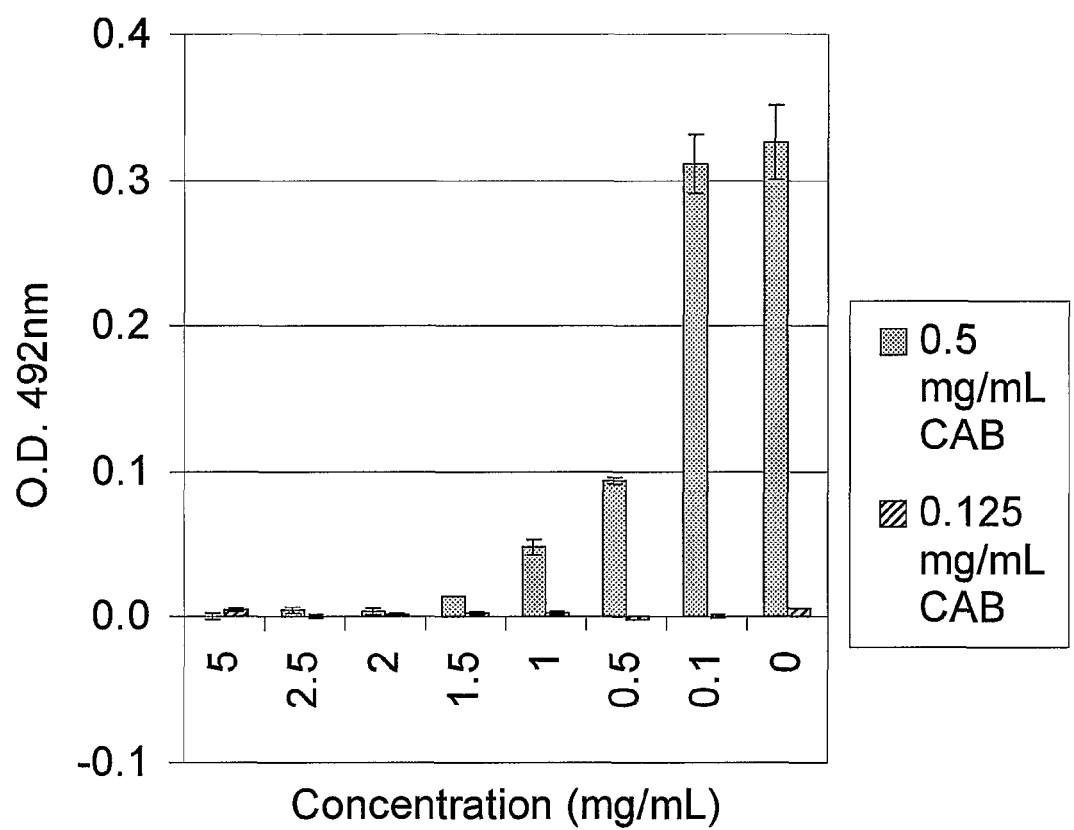

FIG. 2: The effect of alkyl-inulin on the turbidity (absorbance at 492 nm) of refolding CAB solutions after 15 minutes incubation at room temperature.

Figure 3:
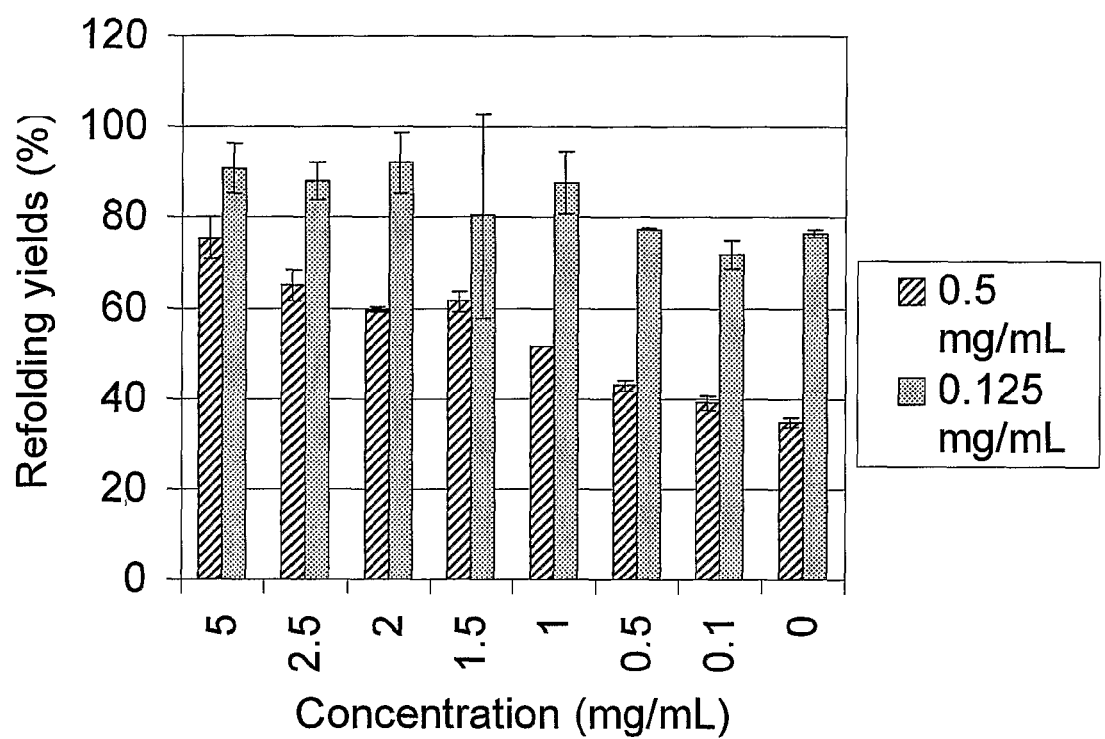

FIG. 3: Refolding yields for two final concentrations of CAB versus alkyl-inulin concentration. The CAB was refolded by 20 fold dilution into alkyl-inulin containing refolding buffer and incubated for 2 hours at room temperature.

Figure 4:
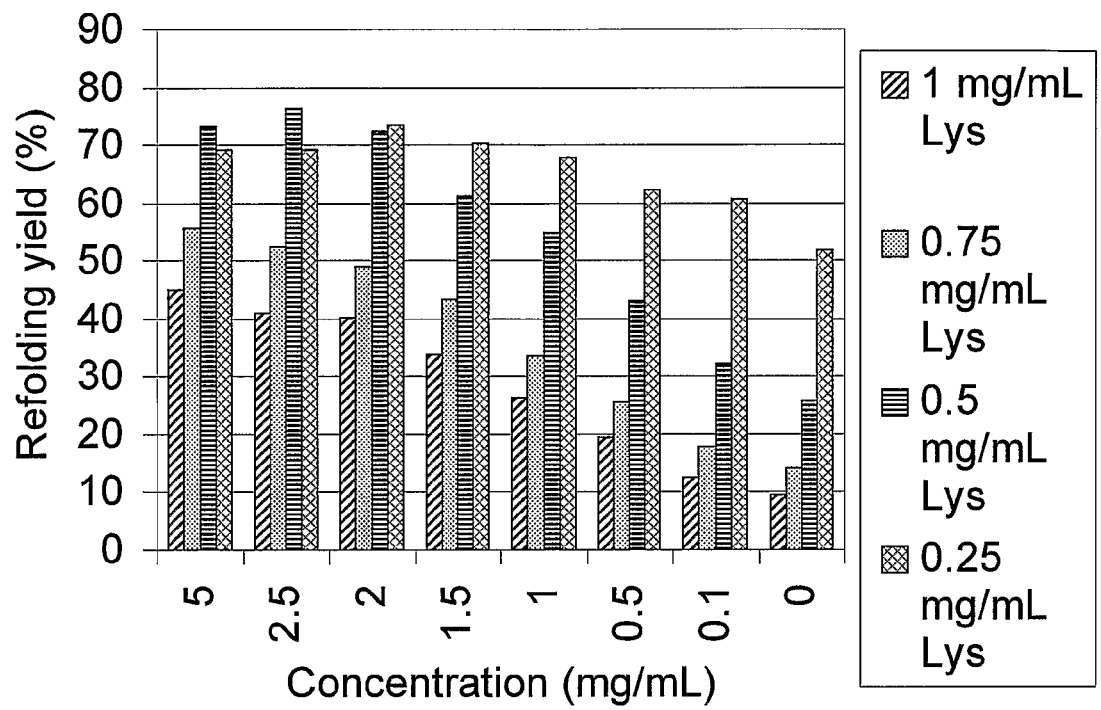

FIG. 4: Refolding yields at four final lysozyme concentrations versus alkyl-inulin concentration. The lysozyme was refolded by 20 fold dilution into refolding buffer containing alkyl-inulin and incubated for 24 hours at room temperature.

Figure 5:
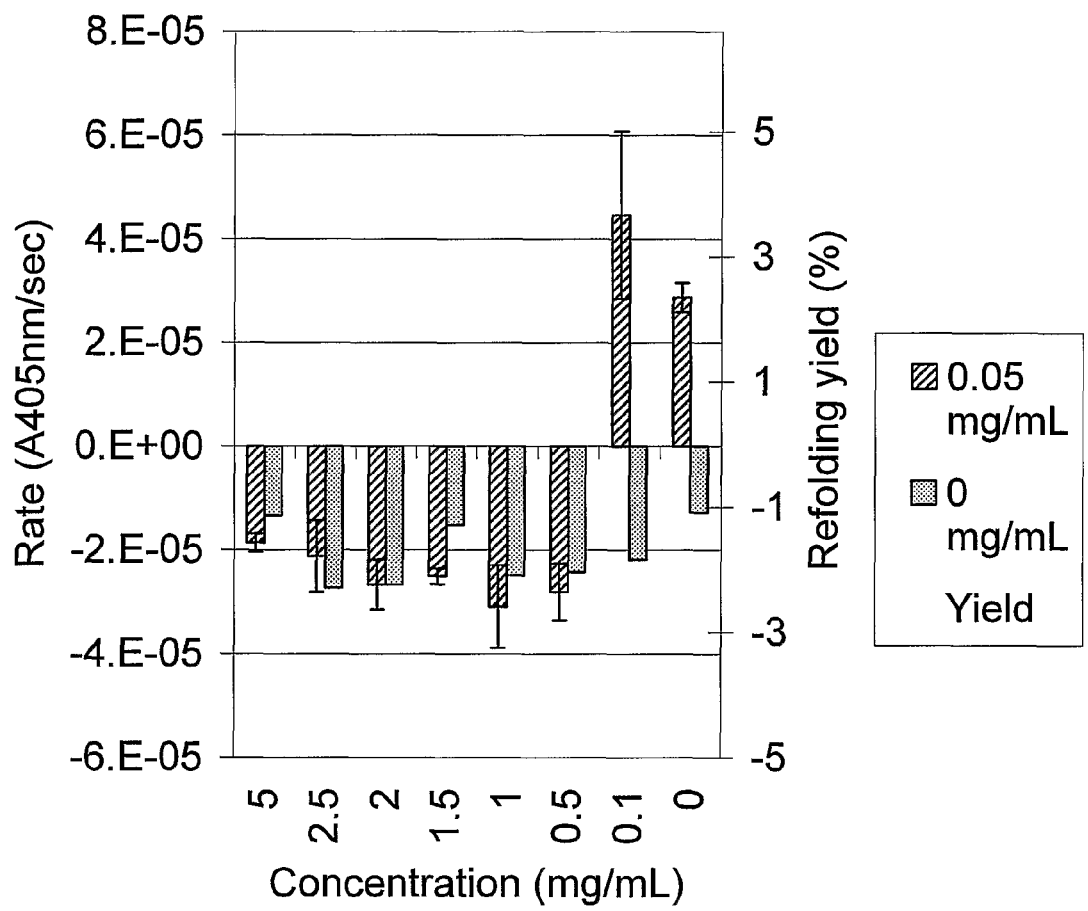

FIG. 5: Refolding yields for CS versus alkyl-inulin concentration. The CS was incubated for 24 hrs at 4° C. followed by a further 72 hr incubation at room temperature. The legend shows the final CS concentration in the refolded and control samples.

Figure 6:
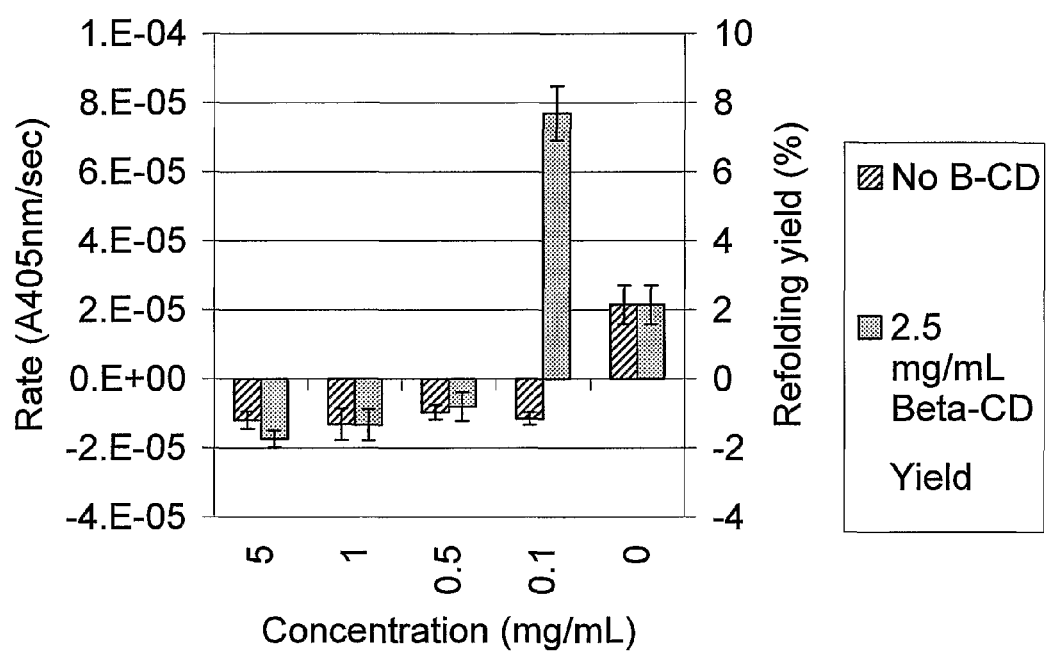

FIG. 6: Refolding yields for CS (0.04 mg/mL final concentration) versus alkyl-inulin concentration. The CS was incubated for 24 hrs at 4° C. followed by a further 72 hr incubation at 4° C. with and without beta-cyclodextrin addition to the refolding buffer. Where beta-cyclodextrin was added after 24 hrs the final beta-cyclodextrin concentration was 2.5 mg/mL.

Figure 7:
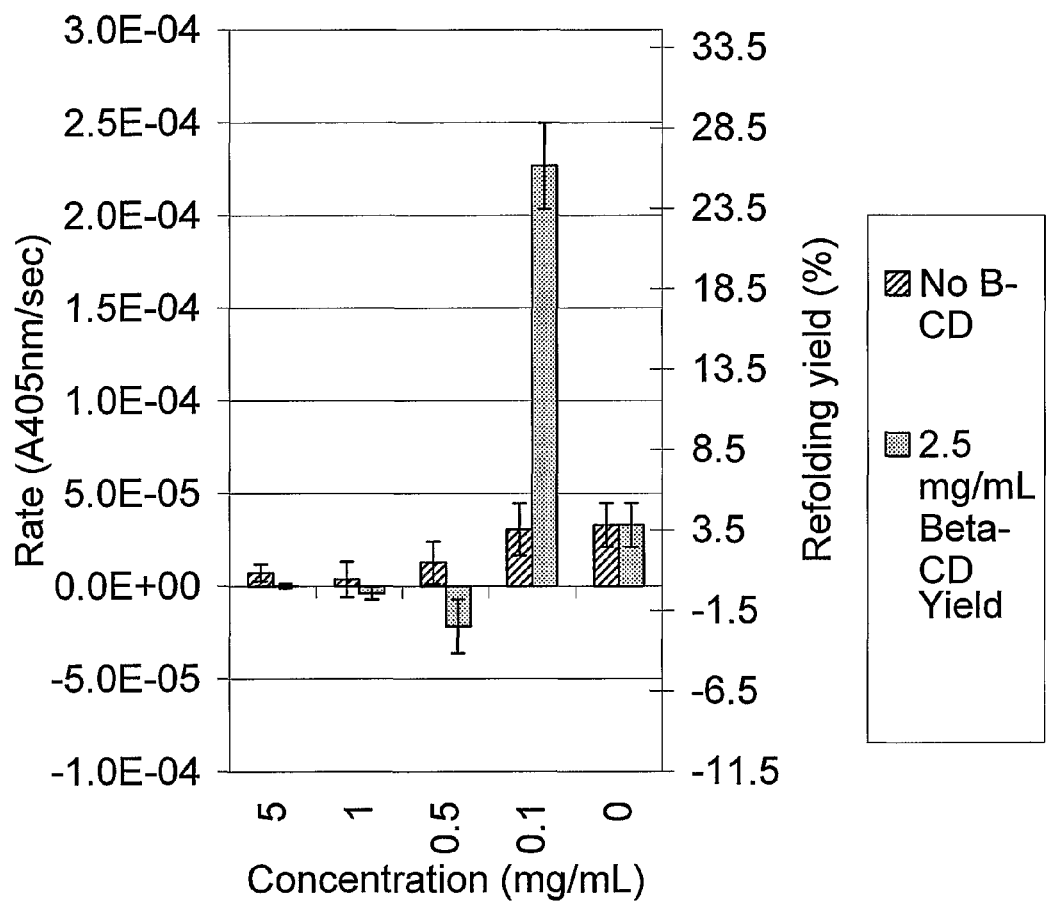

FIG. 7: Refolding yields for CS (0.04 mg/mL final concentration) versus alkyl-inulin concentration. The CS was incubated for 72 hrs at 4° C. followed by a further 12 hr incubation at room temperature. The refolding CS samples were then incubated for a further 8 hrs at 37° C. with and without beta-cyclodextrin addition to the refolding buffer. Where beta-cyclodextrin was added after 24 hrs the final beta-cyclodextrin concentration was 2.5 mg/mL.

It will be understood that the invention is not limited to the embodiments described in the examples and encompasses modifications apparent to those skilled in the art lying within the spirit and scope of the claims appended hereto.

EXAMPLES

Example 1

Refolding Lysozyme Using Inulin (Inutec N®25)

Lysozyme (Fluka 62971) was denatured overnight at 4° C. in 100 mM Tris-HCl buffer at pH 8.1, containing 1 mM EDTA, 8 M urea and 32 mM DTT. The denatured protein (5.0 to 20.0 mg/ml) was diluted 20 times into a refolding buffer (67 mM Tris, 5 mM oxidized glutathione, pH 6.5). In half of the samples, the refolding buffer also contained 10 mg/ml inulin (Inutec N25, Orafti). The reactions were performed in the wells of a 96-well microplate.

The samples were then incubated for 24 hr at room temperature (approx 25° C.) to allow refolding. Lysozyme activity (protein folded to a native, active configuration) was determined by measuring the initial linear rate of decrease in turbidity (absorption at 492 nm) of a *Micrococcus lysodeikticus* (Sigma M-3770) solution. The *Micrococcus* concentration was 0.75 mg/ml in 67 mM sodium phosphate buffer at pH 6.25. The *Micrococcus* solution was mixed with the solution containing the refolded lysozyme in the ratio 10:1 (e.g. 200 μl *Micrococcus* solution, 20 μl refolded lysozyme solution). Standards of native (non-refolded) lysozyme were used to generate a standard curve to calculate the refolding yield.

FIG. 1 shows the refolding yields for lysozyme refolded at a final protein concentration of 0.25 mg/ml in sodium phosphate buffer. In half of the samples, the refolding buffer contained 10 mg/ml inulin. The presence of 10 mg/ml inulin enhanced the refolding yield of the lysozyme compared with the control data where no inulin was present in the refolding buffer.

Example 2

Carbonic Anhydrase (CAB) Refolding Using an Alkyl Inulin Derivative

Carbonic Anhydrase (Sigma C-3934) was denatured overnight at 4° C. in 50 mM Tris-Sulfate buffer at pH 7.8, containing 8 M urea and 32 mM DTT. The denatured protein (2.5-10.0 mg/ml) was refolded by 20 times dilution into a refolding buffer (67 mM sodium phosphate, pH 7.0, containing various concentrations of an alkyl-inulin derivative (Inutec®SP1, also referred to as alkyl-inulin, or SP1) and incubated for 2 hours at room temperature. The carbonic anhydrase activity was determined using a para-Nitrophenol assay and compared with a standard curve created using standards of native carbonic anhydrase at known concentration. The refolded protein samples (or standards) were diluted 10 times with Tris-sulfate buffer at pH 7.8. Para-Nitrophenol was dissolved in a 1:1 water and ethanol solution to a concentration of 10 mM. Five percent by volume of the para-nitrophenol solution was then added to each diluted protein sample and the increase in absorbance at 405 nm was measured. The level of aggregation was assessed by measuring the turbidity (absorbance at 492 nm) of the refolded protein solution.

FIG. 2 shows the turbidity (aggregation level) during a dilution refold of carbonic anhydrase (CAB). In all cases where alkyl-inulin was added to the refolding buffer, the aggregation level was lower than that found in the control sample that did not contain alkyl-inulin. The suppression of aggregation in the solution of folding CAB suggests that a higher proportion of folding-competent CAB monomers are present in solutions in which alkyl-inulin is present. The translation reduced aggregation levels into enhanced refolding yields through the addition of alkyl-inulin to the refolding buffer is shown in FIG. 3. At the higher CAB concentration, where aggregation is a more significant problem, the refolding yield was higher in all instances when cases where alkyl-inulin is present in the refolding buffer compared to the controls in which alkyl inulin was absent. At lower protein concentration the effect was diminished but it was still possible to obtain a significant enhancement of the refolding yield using alkyl-inulin as a refolding additive.

Example 3

Lysozyme Refolding Using an Alkyl Inulin Derivative

Lysozyme (Fluka 62971) was denatured overnight at 4° C. in 100 mM Tris-HCl buffer at pH 8.1, containing 1 mM EDTA, 8 M urea and 32 mM DTT. The denatured protein (5.0 to 20.0 mg/ml) was refolded by dilution 20 times into a refolding buffer (100 mM Tris, 1 mM EDTA, 5 mM oxidized glutathione, pH 8.1). The samples were then incubated for 24 hours at room temperature to allow refolding. Lysozyme activity was determined by measuring the initial linear rate of decrease in turbidity (absorption at 492 nm) of a *Micrococcus lysodeikticus* (Sigma M-3770) solution. The *Micrococcus* concentration was 0.75 mg/ml in 67 mM sodium phosphate buffer at pH 6.25. The *Micrococcus* solution was mixed with the solution containing the refolded lysozyme in the ratio 10:1 (e.g. 200 μl *Micrococcus* solution, 20 μl refolded lysozyme solution). Standards of native lysozyme were used to generate a standard curve to calculate the refolding yield.

FIG. 4 shows the results for lysozyme refolding, four protein concentrations were evaluated. Refolding of lysozyme with alkyl-inulin (as above) in the refolding buffer resulted in improved yield for all the conditions tested, with the largest yield enhancement obtained at the highest protein concentration. The figure shows that lysozyme can be refolded at higher yield or at higher protein concentration (at a fixed yield) when alkyl-inulin is present in the refolding buffer.

Example 4

Citrate Synthase Refolding Using an Alkyl Inulin Derivative

Citrate synthase (Sigma C-3260) was denatured overnight at 4° C. in 67 mM sodium phosphate buffer at pH 7.0, containing 8 M urea and 13 mM DTT. The denatured protein (1.0 mg/ml) was refolded by dilution 20 times into a refolding buffer (67 mM sodium phosphate, pH 7.5, containing various concentrations of the alkyl-inulin) and incubated for various lengths of time at 4° C., room temperature (approx 25° C.) or 37° C., with the optional later addition of beta-cyclodextrin into the refolding mixture. Beta-cyclodextrin addition was performed by adding 20% by volume of a 12.5 mg/mL solution to give a final beta-cyclodextrin concentration of 2.5 mg/mL. The activity of refolded citrate synthase was monitored by the increase in absorbance at 405 nm using an assay to determine the detection of free CoA after the condensation of acetyl-CoA and oxaloacetate by 5,5'dithiobis(2-nitrobenzoic acid) (DTNB). Before analysis, each protein sample was diluted 20 times with deionised water. The diluted protein samples were then contacted with the activity assay reaction mixture in the ratio 1:20 (e.g. 5 µl diluted protein solution, 100 µl reaction mixture). The activity assay reaction mixture consisted of 100 mM Tris-HCl buffer at pH 7.6, containing 1 mM EDTA, 0.1355 mM acetyl-CoA, 0.12 mM DTNB and 0.5 mM oxaloacetate. The refolding yield was calculated through comparison with native citrate synthase samples.

FIG. 5 shows refolding of citrate synthase (CS) in the presence and absence of alkyl-inulin in the refolding buffer. A concentration of 0.1 mg/mL alkyl-inulin resulted in a small increase in the refolding yield compared to the yield detected for control sample that did not contain alkyl-inulin. FIG. 6 shows the results obtained with a two-stage refolding process where the CS was first incubated in a refolding buffer containing alkyl-inulin, followed after 24 hours by a further incubation in the same refolding buffer after the addition of 2.5 mg/mL beta-cyclodextrin. Beta-cyclodextrin addition was performed by adding 20% by volume of a 12.5 mg/mL solution to give a final beta-cyclodextrin concentration of 2.5 mg/mL. Addition of beta-cyclodextrin in the second incubation improved the refolding yield for the samples with 0.1 mg/mL alkyl-inulin in the refolding buffer (c.f. FIG. 5). However, the control samples that did not contain alkyl-inulin did not show improved refolding yield after the addition of beta-cyclodextrin suggesting a synergistic effect between the alkyl-inulin and beta-cyclodextrin rather than a direct enhancement due to beta-cyclodextrin. FIG. 7 shows similar data where the incubation after beta-cyclodextrin addition was conducted at elevated temperature (37° C.). Using an elevated temperature, the refolding yield of CS in buffer containing alkyl-inulin and beta-cyclodextrin could be enhanced beyond that obtained at room temperature (c.f. FIG. 6).

The invention claimed is:

1. A method for folding protein comprising providing an aqueous solution of a protein in non-native conformation and an inulin or inulin derivative or a mixture of inulins and/or inulin derivatives and incubating the solution to permit folding of the protein, wherein the inulin or inulin derivative is a compound of formula (I):

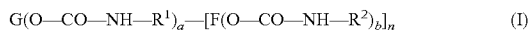

wherein:
G is a terminal glucosyl unit in which one or more hydroxyl groups thereof may be substituted with a group or groups of formula (O—CO—NH—$R^1$);
$R^1$ is selected from the group comprising alkyl groups, alkenyl groups, alkynyl groups, haloalkyl groups, cycloalkyl groups, aryl groups and aralkyl groups and, where there is more than one (O—CO—NH—$R^1$) group on the glucosyl unit, each $R^1$ group may be the same or different;

a is an integer of from 0 to 4;
F is a fructosyl unit in which one or more hydroxyl groups thereof may be substituted with a group or groups of formula (O—CO—NH—$R^2$);
$R^2$ is selected from the group comprising alkyl groups, alkenyl groups, alkynyl groups, haloalkyl groups, cycloalkyl groups, aryl groups and aralkyl groups and, where there is more than one (O—CO—NH—$R^2$) group on the fructosyl unit, each $R^2$ group may be the same or different;
b is an integer of from 0 to 3 for non-terminal fructosyl units and from 0 to 4 for the terminal fructosyl unit;
n is an integer of from 2 to 499,
each unit of formula F(O—CO—NH—$R^2$)$_b$ may be the same or different from any other unit of formula F(O—CO—NH—$R^2$)$_b$; and
the average degree of substitution per glucosyl or fructosyl unit is from 0.01 to 3.0.

2. The method according to claim 1, wherein the inulin or inulin derivative or the mixture of inulins and/or inulin derivatives is present at a concentration of from 0.005 mg/ml to 50 mg/ml.

3. The method according to claim 1, wherein the inulin or inulin derivative or the mixture of inulins and/or inulin derivatives is present at a concentration of from 0.002 mg/ml to 20 mg/ml.

4. The method according to claim 1, wherein incubation is performed at a temperature of from about 0° C. to about 45° C.

5. The method according to claim 1 further comprising removing the inulin or inulin derivative or the mixture of inulins and/or inulin derivatives by dilution, buffer exchange through dialysis, diafiltration, filtration, precipitation and/or a chromatographic method.

6. The method according to claim 5 wherein the inulin or inulin derivative or the mixture of inulins and/or inulin derivatives is removed during and/or after protein refolding.

7. The method according to claim 1 wherein one or more of a chitin, chitosan, cyclodextrin, cycloamylose, hydrophobic resin and/or hydrophobic gel is further included in the solution.

8. The method according to claim 7, further comprising removal of one or more of the chitin, chitosan, cyclodextrin, cycloamylose, a hydrophobic resin and/or a hydrophobic gel from the solution during and/or after protein refolding.

9. The method according to claim 1, wherein said method is preceded by using a chaotrope, detergent and/or reducing agent to denature protein and/or dissolve aggregated proteins and/or inclusion bodies to provide an aqueous solution of protein in non-native conformation.

10. The method according to claim 9, wherein the concentration of chaotrope, detergent and/or reducing agent is reduced prior to, at the start of, or during the method for folding protein by dilution or buffer exchange through dialysis, diafiltration, filtration, precipitation and/or a chromatographic method.

11. The method according to claim 1, wherein a disulphide shuffling agent is included in the folding solution.

12. The method according to claim 1, wherein the inulin or inulin derivative compound of formula (I) is a polydisperse linear or slightly branched inulin N-alkylurethane.

13. A kit designed or suitable for performing a method according to claim 1, comprising, in a container or containers, one or more inulin(s) and/or inulin derivative(s), together with instructions for use of the kit, wherein the one or more inulin(s) and/or inulin derivative(s) is a compound of formula (I):

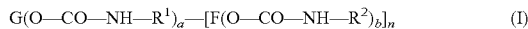
(I)

wherein:
G is a terminal glucosyl unit in which one or more hydroxyl groups thereof may be substituted with a group or groups of formula (O—CO—NH—$R^1$);
$R^1$ is selected from the group comprising alkyl groups, alkenyl groups, alkynyl groups, haloalkyl groups, cycloalkyl groups, aryl groups and aralkyl groups and, where there is more than one (O—CO—NH—$R^1$) group on the glucosyl unit, each $R^1$ group may be the same or different;
a is an integer of from 0 to 4;
F is a fructosyl unit in which one or more hydroxyl groups thereof may be substituted with a group or groups of formula (O—CO—NH—$R^2$);
$R^2$ is selected from the group comprising alkyl groups, alkenyl groups, alkynyl groups, haloalkyl groups, cycloalkyl groups, aryl groups and aralkyl groups and, where there is more than one (O—CO—NH—$R^2$) group on the fructosyl unit, each $R^2$ group may be the same or different;
b is an integer of from 0 to 3 for non-terminal fructosyl units and from 0 to 4 for the terminal fructosyl unit;
n is an integer of from 2 to 499,
each unit of formula F(O—CO—NH—$R^2$)$_b$ may be the same or different from any other unit of formula F(O—CO—NH—$R^2$)$_b$; and
the average degree of substitution per glucosyl or fructosyl unit is from 0.01 to 3.0.

14. The kit according to claim 13, wherein the inulin or inulin derivative compound of formula (I) is a polydisperse linear or slightly branched inulin N-alkylurethane.

15. The kit for performing a method according to claim 1, comprising one or more inulin(s) and/or inulin derivative(s) in a first container or containers and one or more of a cyclodextrin, cycloamylose, chitin, chitosan, hydrophobic resin and/or hydrophobic gel in a second container or containers, optionally together with instructions for use of the kit, wherein the one or more inulin(s) and/or inulin derivative(s) is a compound of formula (I):

(I)

wherein:
G is a terminal glucosyl unit in which one or more hydroxyl groups thereof may be substituted with a group or groups of formula (O—CO—NH—$R^1$);
$R^1$ is selected from the group comprising alkyl groups, alkenyl groups, alkynyl groups, haloalkyl groups, cycloalkyl groups, aryl groups and aralkyl groups and, where there is more than one (O—CO—NH—$R^1$) group on the glucosyl unit, each $R^1$ group may be the same or different; a is an integer of from 0 to 4;
F is a fructosyl unit in which one or more hydroxyl groups thereof may be substituted with a group or groups of formula (O—CO—NH—$R^2$);
$R^2$ is selected from the group comprising alkyl groups, alkenyl groups, alkynyl groups, haloalkyl groups, cycloalkyl groups, aryl groups and aralkyl groups and, where there is more than one (O—CO—NH—$R^2$) group on the fructosyl unit, each $R^2$ group may be the same or different;
b is an integer of from 0 to 3 for non-terminal fructosyl units and from 0 to 4 for the terminal fructosyl unit;
n is an integer of from 2 to 499,
each unit of formula F(O—CO—NH—$R^2$)$_b$ may be the same or different from any other unit of formula F(O—CO—NH—$R^2$)$_b$; and
the average degree of substitution per glucosyl or fructosyl unit is from 0.01 to 3.0.

16. The method according to claim 1, wherein n is an integer of from 2 to 249.

17. The method according to claim 1, wherein n is an integer of from 2 to 99.

18. The method according to claim 1, wherein n is an integer of from 2 to 49.

19. The method according to claim 1, wherein n is an integer of from 9 to 49.

20. The method according to claim 1, wherein n is an integer of from 14 to 39.

21. The method according to claim 1, wherein n is an integer of from 19 to 24.

* * * * *